United States Patent [19]
Ishihara et al.

[11] Patent Number: 5,821,537
[45] Date of Patent: Oct. 13, 1998

[54] INFRARED SPECTROSCOPIC ANALYSIS METHOD FOR GASES AND DEVICE EMPLOYING THE METHOD THEREIN

[75] Inventors: Yoshio Ishihara; Hiroshi Masusaki; Shang-Qian Wu; Koh Matsumoto, all of Tsukuba, Japan

[73] Assignee: Nippon Sanso Corporation, Tokyo, Japan

[21] Appl. No.: 887,262

[22] Filed: Jul. 2, 1997

Related U.S. Application Data

[63] Continuation of Ser. No. 545,580, filed as PCT/JP95/00532 Mar. 22, 1995, Pat. No. 5,703,365.

[30] Foreign Application Priority Data

Mar. 25, 1994 [JP] Japan ..................................... 6-056334
Mar. 25, 1994 [JP] Japan ..................................... 6-056335
Jan. 17, 1995 [JP] Japan ..................................... 7-005329

[51] Int. Cl.$^6$ .................................................. G01N 21/35
[52] U.S. Cl. ....................................................... 250/339.13
[58] Field of Search ........................................ 250/339.13

[56] References Cited

U.S. PATENT DOCUMENTS 5,317,156  5/1994  Cooper et al. .......................... 250/345

Primary Examiner—Constantine Hannaher
Attorney, Agent, or Firm—Oblon, Spivak, McClelland, Maier & Neustadt, P.C.

[57] ABSTRACT

A device and method for measuring an impurity in a trace concentration in a gas to be measured by infrared spectroscopic analysis employing a diode laser are provided. In order to carry out analysis with high sensitivity and high accuracy, the gas to be measured is directed into sample cell 5 and placed in a low pressure state by a pump 16. Infrared light from the wavelength region in which strong absorption peaks from the impurity can be obtained are oscillated from the diode laser 1, and a derivative absorption spectrum is measured by passing the infrared rays through sample cell 5 and reference cell 8 which is filled with the impurity alone. The spectrum for the gas to be measured and the spectrum for the impurity alone are compared, and the impurity is identified by confirming a plurality of absorption peaks originating from the impurity. Determination of the impurity is then carried out from absorption intensity of the strongest peak. In the case where molecules of the gaseous impurity form clusters in the gas to be measured, analysis is carried while dissociating the clusters by irradiating light having a photon energy of 0.5 eV or greater. The device and method are particularly suitable for carrying out analysis of trace quantities of impurities present in the gases which are used as materials for semiconductor manufacturing.

12 Claims, 22 Drawing Sheets

INFRARED SPECTROSCOPIC ANALYSIS METHOD FOR GASES AND DEVICE EMPLOYING THE METHOD THEREIN

This is a Continuation of application Ser. No. 08/545,580 filed on Nov. 20, 1995, now U.S. Pat. No. 5,703,365, which is a 371 application of PCT/JP95/00523 filed on Mar. 22, 1995.

TECHNICAL FIELD

The present invention relates to a method for analyzing trace amounts of a component which is included in a gas to be measured by means of infrared spectroscopic analysis employing a diode laser as the light source, and to a device which employs the method therein.

BACKGROUND ART

Infrared spectroscopic analysis is frequently used as a method for analyzing a gaseous test material. A simple explanation will now be made of the principle of infrared spectroscopic analysis. In polyatomic molecules, each molecule has its own vibration energy level corresponding to the bonds between the atoms which make up the molecules. For this reason, when the molecules are exposed to electromagnetic waves of a wavelength which has a photon energy equivalent to the value of their vibration energy level, the molecules absorb the electromagnetic waves as their own vibration energy. The amount of absorption, moreover, is proportionate to the abundance of the molecules present. When this vibration energy level value is converted to photon energy, ordinarily, it will correspond to wavelengths in the infrared region.

Accordingly, in infrared spectroscopic analysis, light in the infrared region is passed through the gas to be measured and the absorption spectrum is measured. Analysis is carried out by analyzing the absorption spectrum. Identification within the gas to be measured of gaseous molecules (impurity) targeted for measurement here can be made from the wavelength of the light absorbed. A quantitative determination of those molecules can then be made from the absorbance.

For example, in the semiconductor industry, various types of gases are used as the material for semiconductors. In Very-Large-Scale-Integration manufacturing processes, impurities such as moisture, for example, are damaging if present in even extremely trace amounts in the semiconductor material gases. Accordingly, reducing and controlling impurities in the semiconductor material gas is an important aspect of production control.

The present applicants previously submitted a patent application (Japanese Patent Application, Laid-Open No. Hei 5-99845) for an invention relating to a method for measuring the moisture in a gas using a tunable InGaAsP diode laser which oscillates in the region of wavelength 1.3 to 1.55 $\mu$m.

The device for analysis of the moisture recorded in this publication is provided with a diode laser which oscillates in the region of wavelength from 1.3 to 1.55 $\mu$m at room temperature; a measurement line which causes the laser light oscillated at room temperature from the diode laser to branch, guides it into a gas cell used for measurement, and then sends it on to a light detector for measurement use; a reference line which causes the aforementioned laser light to branch, guides it into a gas cell used for reference, and then sends it on to a light detector for reference use; and a power monitor line which causes the aforementioned laser light to branch and sends it on to a light detector which is used as a power monitor. The device is designed to employ as the aforementioned detectors, light detectors which are sensitive to light in the region of wavelength from 1.3 to 1.55 $\mu$m at room temperature.

In the method for measuring moisture using this device, the laser oscillating wavelength is scanned by means of varying the injection current to the diode laser, and the absorption spectrum is measured. For example, the absorption peak for $H_2O$ which is in the region of wavelength of 1.38 $\mu$m is selected, and the water vapor concentration in the gas is measured using the absorption intensity and a calibration curve made in advance. The application of this method, which permits easy in-situ measurement and is useful as a process monitor in the production control process, was anticipated for analysis of semiconductor material gases.

Examples of the absorption spectrum disclosed in the above publications are shown in FIGS. 22 and 23. FIG. 22 is an absorption spectrum for the case where the gas component is $H_2O$ only, while FIG. 23 is the absorption spectrum for a test material containing $H_2O$ in nitrogen gas. The absorption intensity (peak height) obtained here is measured and the concentration of the moisture is obtained from the calibration curve (shown in FIG. 24) which was made in advance.

As shown in the graph, four absorption peaks originated with $H_2O$ are observed in FIG. 22. Further, in the nitrogen gas based test material in FIG. 23, one broad absorption band is observed, however, absorption in this wavelength region is not due to nitrogen gas, nor is it believed to be a product of reaction between the nitrogen and the moisture. Accordingly, the broad absorption band in FIG. 23 is believed to be the result of the overlap of the four closely located individual peaks in FIG. 22, causing the formation of one absorption band.

In this way, if the method disclosed in the aforementioned patent application 5-99845 is used without modification to analyze impurities in semiconductor material gas, the sensitivity of detection is not very high even in the case where the absorption peaks arising from the impurity do not experience interference from nearby peaks arising from the gas to be measured.

Further, depending on the type of gas to be measured and the type of impurity for which measurement is being attempted, absorption peaks originating from the semiconductor material gas may be present near the absorption peaks originating from impurities such as moisture or the like. In this case, as a result of the overlapping of nearby peaks, the accuracy of measurement becomes poor. For this reason, the above method is unsatisfactory for the analysis of trace amounts of an impurity in a semiconductor material gas where a high degree of accuracy is demanded.

For ease of operation and in order to obtain absorption of sufficient intensity by the target gas being measured (that is, the impurity), measurements were carried out with the pressure of the gas to be measured at around one atmospheric pressure or more in the infrared spectroscopic analysis. This is also true for the method disclosed in patent application 5-99845.

When the concentration of the target gas being measured (impurity) in the gas to be measured is high, no problems occurred particularly even when measuring at these kinds of pressures.

However, in infrared spectroscopic analysis, when the pressure of the gas to be measured is high, in general the width of the absorption peak lines arising from the impurity becomes broad. For this reason, when the concentration of the impurity in the gas to be measured is low, the resolution of the absorption peaks decreases, and the accuracy of measurement becomes poor.

SUMMARY OF THE INVENTION

The present invention was conceived to resolve the aforementioned problems, and has as its objective the provision of a device and method wherein a trace impurity concentration in a gas to be measured can be analyzed with high sensitivity and accuracy in an infrared spectroscopic analysis which employs a diode laser.

The present invention's infrared spectroscopic analysis method for gas attempts to resolve the aforementioned problems by carrying analysis of the gas to be measured under a low pressure state in a method for analyzing the impurity in the gas to be measured by passing light from the infrared region through the gas to be measured and measuring the intensity of absorption. By lowering the pressure of the gas to be measured, it is possible to improve the resolution of the peaks of the absorption spectrum.

The desirable pressure range for the gas to be measured may be varied according to the resolution demanded or the type of impurity which is the target of measurement. However, if the pressure is set in the range of 10 to 500 Torr, good sensitivity and accuracy can be obtained.

In the method of the present invention, it is preferable to measure the absorption spectrum by scanning the wavelength of light which is to be passed through the gas to be measured. The wavelength range of the light to be swept is preferably selected within the range for which it is possible to obtain a strong absorption peak for the impurity. For example, the wavelength may be preferably selected to be in the range of 1.19 to 2.00 $\mu$m.

In a method using an absorption spectrum to identify and determine the impurity in a gas to be measured, it is desirable to compare the absorption spectrum for the gas to be measured and an absorption spectrum measured separately and obtained for the impurity alone in order to identify the impurity by confirming the presence of a plurality of absorption peaks originating from the impurity, and to then select from this plurality of peaks the strongest peak not experiencing interference from nearby peaks and to determine the impurity from the absorption intensity of this strongest peak.

At this point, the absorption spectrum can be measured by passing light through the gas to be measured, while an absorption spectrum may simultaneously be measured by passing light of the same wavelength through the impurity alone.

Detection sensitivity can be improved if the derivative absorption peak obtained by detecting the derivative of change in the absorption intensity is used as the aforementioned absorption peak.

Further, identification can be carried out with accuracy if the impurity is identified from the relative intensities of the plurality of absorption peaks.

In the method of the present invention, when molecules of a gaseous impurity form clusters in the gas to be measured, it is desirable to dissociate these clusters and then carry out the analysis, making it possible to stabilize and carry out an accurate analysis.

Clusters can be dissociated by irradiating the gas to be measured with light having a photon energy of 0.5 eV or greater and then carrying out analysis.

Further, when setting the photon flux density with respect to the gas to be measured of the aforementioned light having a photon energy of 0.5 eV or greater to $D_p$ (photon number/sec·cm$^2$), and the density of molecules in the gas to be measured to N, it is preferable that $D_p \geq N/2$.

Further, the infrared spectroscopic analysis device of the present invention is provided with a wavelength tunable diode laser that oscillates in the infrared region, a means for passing light oscillated from the laser through the gas to be measured, and a means for measuring the intensity of the laser light which has passed through the gas to be measured, the device using infrared spectroscopy to analyze the impurity in the gas to be measured, and being characterized by the provision of a means for lowering the pressure of the gas to be measured.

The absorption spectrum of the gas to be measured and the absorption spectrum for the impurity alone can be obtained simultaneously provided that the device is one equipped with a means for branching the light oscillated from the diode laser and passing one portion of the branched light through the gas to be measured while passing the other portion of the branched light through the impurity alone, a means for measuring the absorption spectrum of the light passed through the gas to be measured, and a means for measuring the absorption spectrum of the light which passed through the impurity alone. For this reason, an accurate comparison of these absorption spectrums can be made.

Further, if the device is one provided with a means for measuring a derivative absorption spectrum by detecting the derivative change in absorption intensity, the derivative value absorption peak can be used in the measurement of the impurity, making it possible to improve detection sensitivity.

Additionally, analysis of an impurity can be carried out quickly if the device is provided with a means wherein the absorption spectrum of light passed through the gas to be measured and the absorption spectrum of light passed through the impurity alone are compared, an absorption peak having an absorption wavelength that coincides with the absorption peak of the absorption spectrum of the light passed through the gaseous impurity alone is recognized from among the absorption peaks of the absorption spectrum of the light passed through the gas to be measured; and the absorption intensity of this absorption peaks is detected.

If a means for irradiating the gas to be measured with light having a photon energy of 0.5 eV or greater is provided, clusters can be dissociated and analysis then carried out, even in the case where the clusters formed by the impurity in the gas to be measured cannot be disassociated using the light source.

PREFERRED EMBODIMENTS OF THE PRESENT INVENTION

Figure 1:
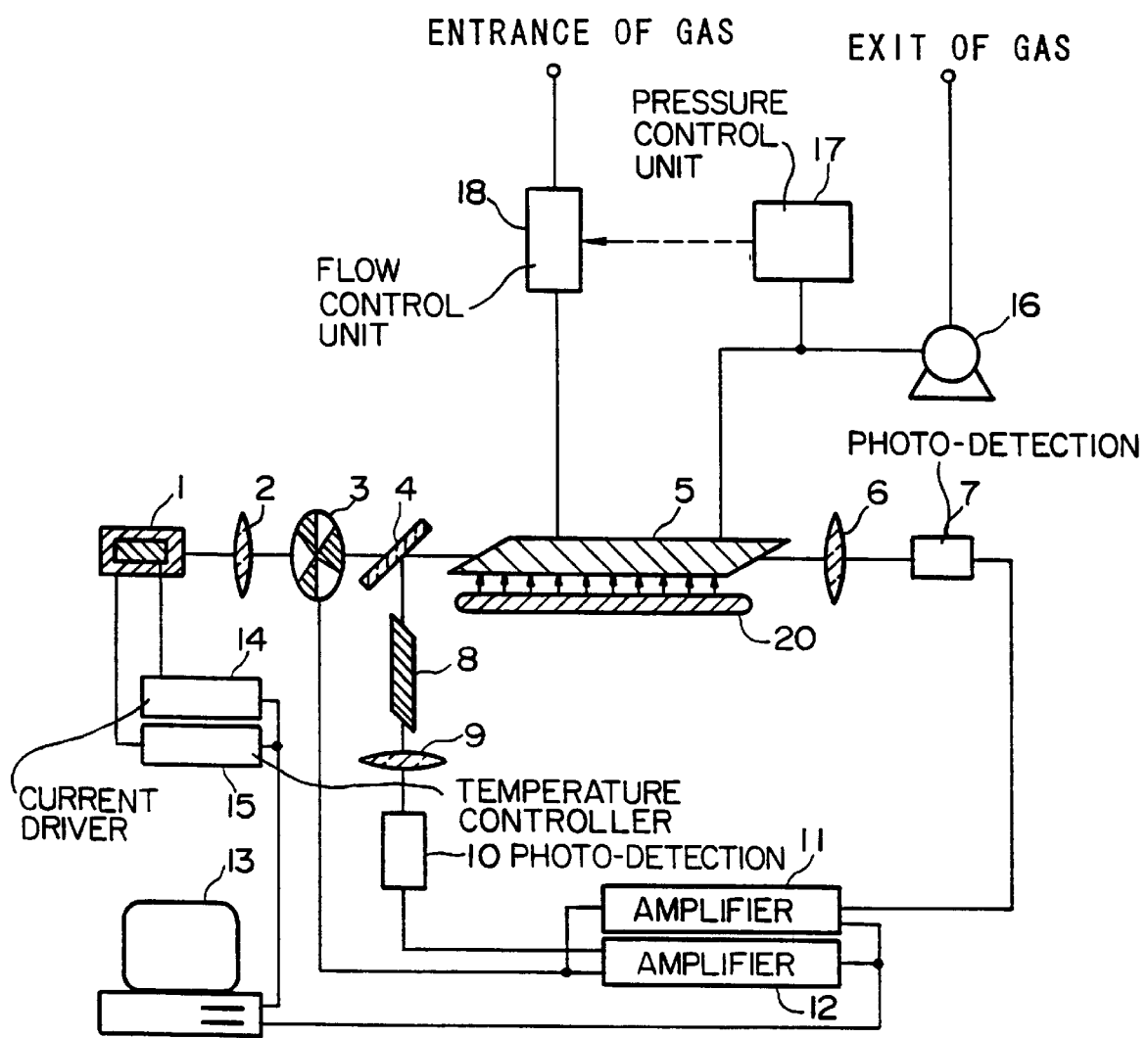
FIG. 1 is a structural diagram showing an embodiment of the infrared spectroscopic analysis device of the present invention.

The present inventors investigated various means for improving the resolution of absorption peaks in infrared spectroscopic analysis.

First, pressure at time of measurement was studied. In general, when the pressure of the gas in infrared absorption is high, the absorption peak broadens due to the influence of molecular collision. The width of the peak becomes broad and resolution decreases. When the pressure of the gas is lowered, the intensity of absorption decreases. The width of the peak becomes narrow and resolution improves. Accordingly, in the present invention, by carrying out infrared spectroscopic analysis with the gas under low pressure, it is possible to measure the impurity included in the gas with higher sensitivity and accuracy.

Additionally, in contrast to the conventional art wherein measurement was carried out with the gas to be measured at around one atmospheric pressure or higher, the present invention improves the accuracy of measurement by reducing pressure. Accordingly, the low pressure state referred to in the present invention indicates a state wherein the total pressure of the gas to be measured is less than one atmospheric pressure.

In general, if the pressure of the gas to be measured is large, namely in the range of 500 Torr or more, the width of the absorption peak becomes broad. Accordingly, the height of the absorption peak becomes small. Thus, in the case where the amount of an impurity which is the target of measurement is trace, when the pressure is too large, the peak broadens and resolution decreases. On the other hand, when the pressure of the gas to be measured is less than 500 Torr, the width of the absorption peaks becomes narrow accompanying the decrease in pressure (the absorption peak becomes higher). This decrease in the width of the absorption peaks, however, is not without limits. In other words, the width approaches a fixed value unrelated to the pressure, that is to say, the Doppler limit, based on the Doppler effect. Accordingly, if pressure is reduced too low, the decrease in the width of the absorption peak becomes dulled, and its height becomes low. As a result, the sensitivity of detection decreases.

Accordingly, it was realized that, when measuring trace quantities of an impurity included in a gas to be measured, if the total pressure of the gas to be measured is set within the range of 10 to 500 Torr, good measurement sensitivity and measurement accuracy can be obtained. The preferred degree of pressure reduction can be set according to the type of impurity present and the level of resolution required.

Further, when the impurity is present in trace amounts, the amount of light absorbed by the impurity is small with respect to the amount of light incidented on the gas to be measured, so that the signal-to-noise ratio becomes very small. By using the rate of change in the amount of absorption, that is by detecting the derivative value for the change in absorption intensity and using the derivative absorption peak, the sensitivity of measurement can be improved. In this case, the preferred level of pressure reduction can similarly be set to 10 to 500 Torr.

Namely, in order to obtain a derivative absorption spectrum, a frequency modulation method which injects current $i=I_0+a \cdot \sin(\omega t)$ to the diode laser, that is, the AC component $a \cdot \sin(\omega t)$ coupled with the DC component $I_0$, can be used. Because, at this point, the width of the derivative absorption peak is broad with increasing the pressure of the gas to be measured, modulation amplitude "a" becomes large in response to this. Noise also becomes large accompanying this. An upper limit for the optimum pressure when conducting measurements is determined for this reason. However, when the pressure of the gas to be measured is lowered, reaching the Doppler limit region, the height of the derivative absorption peak becomes low, and detection sensitivity decreases. For this reason, an optimal lower pressure limit for measurement is determined.

Investigations were next made of the range of wavelengths to be measured. In the present invention, the accuracy of analysis can be improved by selecting a wavelength range wherein absorption peaks from the impurity (target gas of measurement) can be obtained and where a strong peak can be obtained.

Of the impurities in a semiconductor material gas, $H_2O$ molecules have the largest effect. For this reason, the following examples will begin by illustrating the case where $H_2O$ molecules are the impurity targeted for measurement.

$H_2O$ molecules display very many absorption peaks over a wide wavelength region. In particular, it is preferable to select the wavelength region to be in the range of 1.35 to 1.42 $\mu$m where the absorption cross section from $H_2O$ molecules is at least one order of magnitude larger than that of other near-infrared regions.

Effective wavelength regions for detecting other gaseous impurities which are the target of measurement are as follows:

| | |
|---|---|
| carbon dioxide ($CO_2$) | 1.43 to 1.46 $\mu$m |
| hydrogen fluoride (HF) | 1.25 to 1.35 $\mu$m |
| methane ($CH_4$) | 1.29 to 1.50 $\mu$m |
| mono-silane ($SiH_4$) | 1.19 to 2.00 $\mu$m |
| hydrogen bromine (HBr) | 1.34 to 1.37 $\mu$m |
| hydroxyl group (—OH) | 1.40 to 1.45 $\mu$m |

Further, in the present invention, the identification of the impurity in the gas to be measured from the obtained absorption spectrum may be carried out by measuring the absorption spectrum for the impurity alone in a separate process and confirming the plurality of absorption peaks originating from the impurity. As a result, it is possible to carry out an accurate identification.

When the identification is being carried out in this way, if the relative intensities of the plurality of peaks is employed, it is possible to identify the impurity with surety. Thus, it is possible to improve measurement sensitivity and measurement accuracy.

The determination of the identified impurity may be carried out by selecting the strongest peak not experiencing interference from nearby peaks from among the plurality of absorption peaks used in the identification, and carrying out determination of the impurity from the intensity of absorption of this strongest peak. In this manner, it is possible to carry out an accurate measurement.

Further, the measurement of the absorption intensity may be carried out by using not only the spectrum for the amount of absorption, but also the rate of change in the amount of absorption; that is, the derivative absorption spectrum of the change in absorption intensity, by which it is possible to improve measurement sensitivity. In order to obtain the derivative absorption spectrum, the aforementioned frequency modulation method can be employed.

In this way, by carrying out measurement by selecting an optimal low pressure state and wavelength range with respect to the impurity, the accuracy of the measurement can be improved. However, realizing that wavelength at which an absorption peak is obtained can shift, and the peak's absorption intensity can vary depending on the type of gas to be measured in which the impurity is contained and on the light intensity of the laser at time of measurement, the present inventors carried out further investigations.

Figure 2:
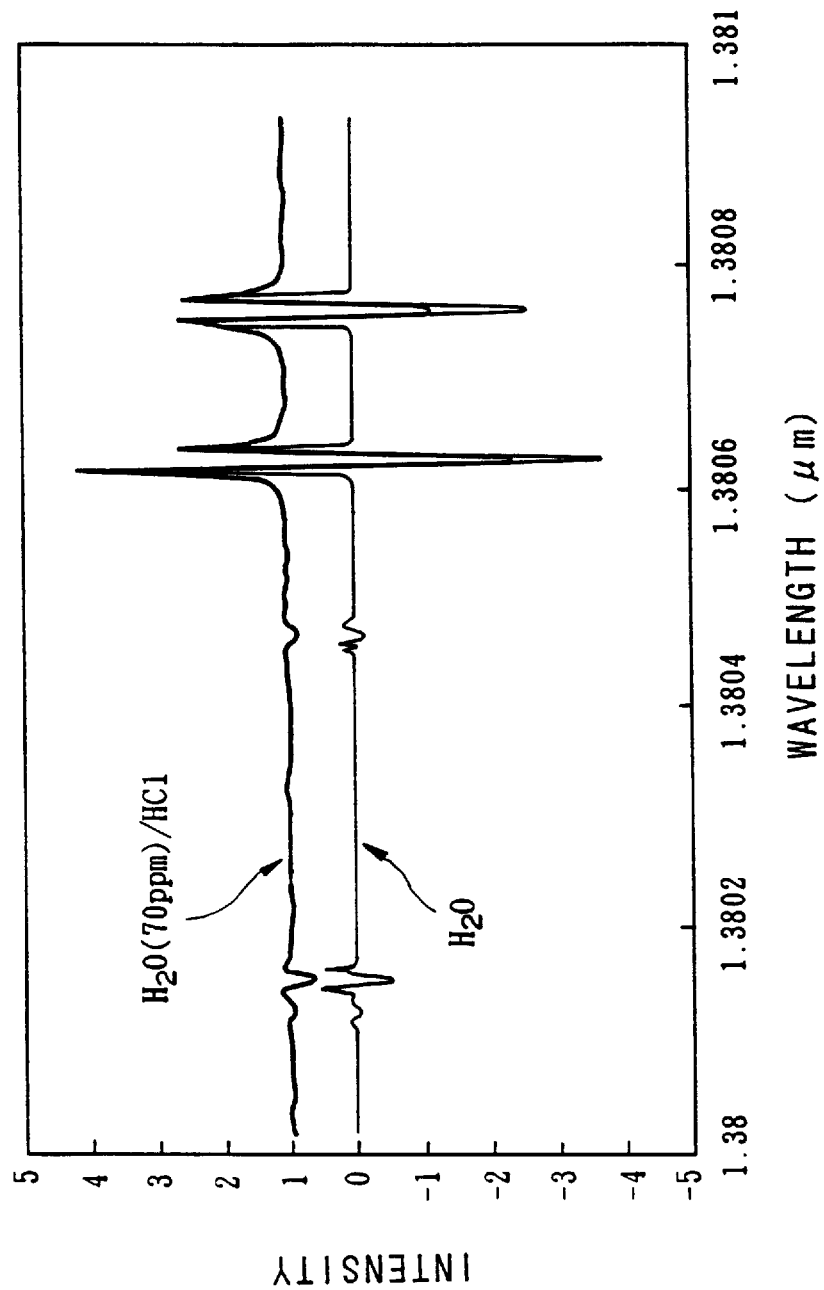
FIG. 2 is an example of a derivative absorption spectrum originating from $H_2O$ which was measured using the method of the present invention.

FIG. 2 is a graph showing an example of the results of infrared spectroscopic analysis of a gas under low pressure (100 Torr), the hydrogen chloride (HCl) gas including moisture in the amount of 70 ppm. The graph is a derivative absorption spectrum of the change in absorption intensity. Additionally, infrared spectroscopic analysis of $H_2O$ under a pressure of 20 Torr was simultaneously carried out in the same way.

In FIG. 2, oscillation wavelength is noted on the horizontal axis while the derivative of the change in absorption intensity is noted on the vertical axis. Further, in order to avoid overlap between the spectrum for the moisture component alone (indicated in the figure by the thin line) and the spectrum for the sample gas (indicated in the figure by the thick line), the base line of the sample gas spectrum was raised by one scale unit.

As can be observed in FIG. 2, there is good coincidence of absorption intensity (amount of absorption) of four absorption peaks between the spectrum of the moisture alone and the sample gas spectrum where in the moisture is contained in hydrogen chloride. Furthermore, there is good coincidence of the position (wavelength) of four sharp absorption peaks between the spectrum for the moisture alone and the sample gas spectrum where the moisture is contained in hydrogen chloride.

Figure 3:
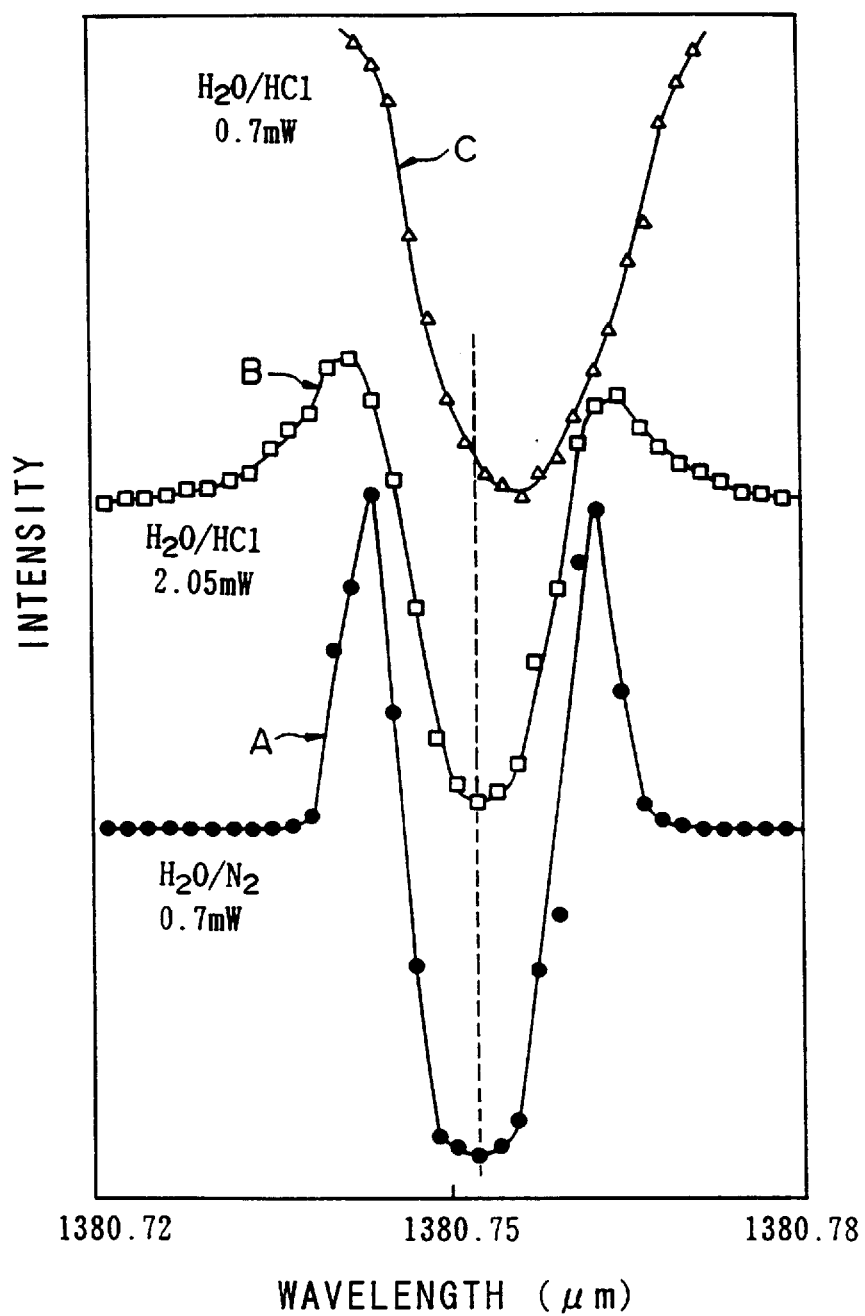
FIG. 3 is a graph for explaining the displacement of the absorption peak wavelength as a result of the formation of clusters.

However, when absorption peaks near wavelength 1.38075 $\mu$m obtained in FIG. 2 are examined more closely, for example, it can be understood that this absorption peak position (wavelength) shifts according to the measurement conditions, as is shown in FIG. 3.

In FIG. 3, A indicates the case where $H_2O$ in nitrogen ($N_2$) is measured at a laser light power of 0.7 mW; B indicates the case where $H_2O$ in hydrogen chloride (HCl) is measured at a laser light power of 2.05 mW; and C indicates the case where $H_2O$ in hydrogen chloride (HCl) is measured at a laser light power of 0.7 mW. Additionally, the pressure of the gas to be measured in all cases was 100 Torr.

Further, in FIG. 3, the broken line indicates the standard position of the $H_2O$ peak obtained using a reference cell.

As shown here, in the case indicated by B wherein the $H_2O$ in HCl gas was measured using high power laser light, the absorption peak wavelength coincides with the standard position. In contrast, in the case of C where measurement was conducted using low power laser light, a shift toward the red occurs away from the standard position.

Furthermore, despite the fact that in the case of A, the $H_2O$ in $N_2$ was measured using a low power laser light in the same way performed in C, the absorption peak wavelength coincided with the standard position.

Figure 4:
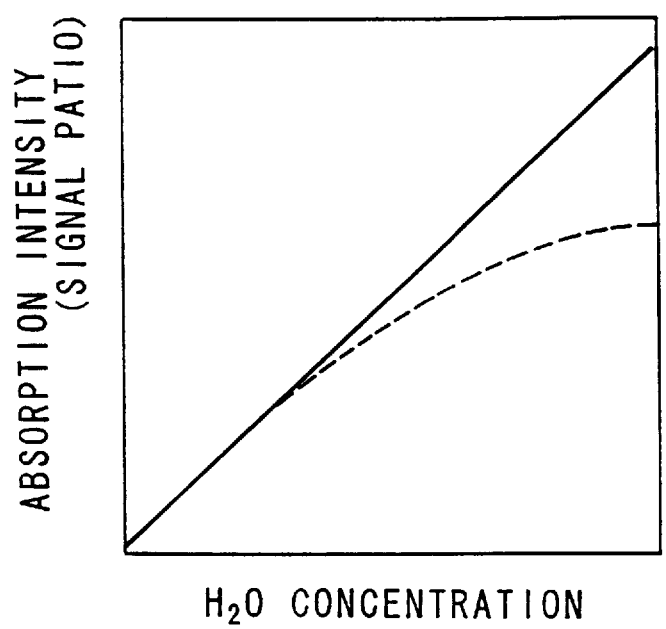
FIG. 4 is a graph for explaining the non-linearity between the absorption peak intensity and the water concentration as a result of formation of clusters.

FIG. 4 shows the relationship between the concentration of $H_2O$ in HCl and absorption intensity. The solid line indicates measurement at a laser light power of 2.05 mW, while the broken line indicates measurement at a laser light power of 0.7 mW. As shown here, when the laser light power is 2.05 mW, a good linear relationship is displayed between $H_2O$ concentration and absorption intensity, and the graph obtained can be used as a calibration curve. However, when the laser light power is set to the small value of 0.7 mW, the deviation from a straight line becomes larger as the concentration of $H_2O$ increases. Accordingly, the graph obtained cannot be used as a calibration curve.

In this way, then, if the laser light power at the time of measurement is not appropriate, the absorption peak wavelength experiences a shift away from the standard position. Accordingly, when absorption peaks from other components lie near the shifted absorption peak wavelength, it becomes difficult to make a qualitative identification. Further, because the absorption peak wavelength shifts while at the same time quantity of absorption changes, an accurate calibration curve cannot be obtained, making it impossible to make an accurate determination.

As a result of extensive research on the cause of absorption peak wavelength shifts such as shown in FIG. 3 and the non-linearity phenomenon such as shown in FIG. 4, the present inventors realized that the cause lay in the formation of clusters by the molecules of impurity in the gas to be measured.

In other words, there are many molecules such as water ($H_2O$), hydrogen chloride (HCl) and ammonia ($NH_3$) which are strongly polar. For example, in HCl, both the positively charged hydrogen atoms and the negatively charged chlorine atoms have electrifications and are strongly polar. It is known that the molecules of this type of strongly polar gas form bonds as a result of Coulomb force with each other and, of course, with non-polar molecules, giving rise to the formation of clusters consisting of a plurality of molecules.

Namely, in C of FIG. 3, the HCl which is the gas to be measured and the $H_2O$ which is the impurity are both strongly polar molecules. The HCl and $H_2O$ molecules are believed to form clusters by bonding together. In contrast, in A in FIG. 3, the nitrogen which is the gas to be measured is a non-polar molecule. In this case, even if the impurity is the strongly polar molecule $H_2O$, because it is present in a trace amount, the $H_2O$ molecules are not believed to form clusters with $N_2$ in the $N_2$ gas.

In conventional gas spectral analysis methods, little attention was given to the formation of clusters such as described above. When the present inventors carried out spectral analysis of a gas in which clusters had formed, it was discovered that the absorption peak wavelength shifted from the standard position and the absorption intensity changed depending on the measurement conditions.

Accordingly, the present invention was designed to enable the carrying out of an accurate analysis by dissociating clusters formed by the molecules of an impurity in the gas to be measured, and then carrying out spectral analysis.

As a method of dissociating clusters, there is the method of irradiating with a light energy which is greater than the energy for cluster formation. More concretely, the energy for cluster formation is less than 0.5 eV. Accordingly, by irradiating the gas to be measured with a photon energy that is 0.5 eV or greater, a state wherein the clusters are dissociated can be obtained.

The wavelength of light having a photon energy of 0.5 eV is 2.48 $\mu$m. Accordingly, when light of wavelength 2.48 $\mu$m or less is used in spectral analysis, it is possible for the irradiation light for spectral analysis to also serve as the irradiation light for cluster dissociation. However, when the wavelength of the irradiation light used for spectral analysis is longer than 2.48 $\mu$m, light of wavelength of 2.48 $\mu$m or less may be used additionally to accomplish cluster dissociation.

Further, the efficiency of cluster dissociation using irradiation by light having a photon energy of 0.5 eV or greater varies accordingly to the pressure of the gas to be measured and power of the irradiation light. For example, when the pressure of the gas to be measured is large, the efficiency becomes poor and it is necessary to increase the power of the irradiation light. If the power of the irradiation light is made high, the degree of cluster dissociation becomes large. In the present invention, however, dissociation of clusters may be carried out to the extent that there is no hindrance presented to the process of spectral analysis. In order to do this, when $D_p$ (photon number/sec·$cm^2$) is the photon flux density with respect to the gas to be measured of the light with a photon energy of 0.5 eV or greater, and when N (molecules) is the density of gas molecules in the gas to be measured, it is desirable that $D_p$ and N satisfy the equation $D_p \geq N/2$.

Irradiating photon energy in this way is an effective method to use when molecules of the impurity in the gas to be measured form clusters. While it is not necessary to use this type of light energy irradiation when it is clear that the molecules of the impurity do not form clusters because of the composition of the gas to be measured, etc., use of this technique in any case will not present a problem.

In the present invention the type of gas to be measured is not particularly limited, but rather appropriately used are various gases such as general gases like nitrogen, oxygen, argon, helium, carbon dioxide and the like, or semiconductor material gases such as silane, phosphine, arsine, trichlorosilane, hydrogen chloride or organometallic compounds.

Moreover, provided that the impurity that is the target gas to be measured in the present invention is a substance on which infrared spectroscopic analysis can be performed, then the present invention can be appropriately applied to the analysis of inorganic compounds such as water, carbon dioxide, carbon monoxide, hydrogen fluoride, hydrogen chloride, hydrogen bromide, hydrogen iodide, mono-silane ($SiH_4$), and many such organic compounds as methane.

EMBODIMENTS

Preferred embodiments of the present invention follow below. The present invention, however, is not limited to these embodiments but rather may be applied to the analysis of a variety of gases.

FIG. 1 is a schematic structural diagram showing an embodiment of the infrared spectroscopic analysis device of the present invention.

In this device, light from diode laser 1, the light source, is collimated at lens system 2, undergoes chopping at chopper 3, passes through half mirror 4 and is divided into two sets of light rays. One set of light rays passes through sample cell 5, is focused by focusing lens 6 and enters into photo-detection device 7. The other set of light rays passes through reference cell 8, is focused by lens 9 and enters into photo-detection device 10. The target substance to be measured is inside reference cell 8 under reduced pressure. The light which is in detection devices 7 and 10 is converted to an electric signal and sent to phase-sensitive amplifiers 11 and 12, respectively. At phase-sensitive amplifiers 11 and 12, a signal in synchronization with the modulation signal sent from chopper 3 is amplified, enters calculator 13, and is processed as measurement data. The current of diode laser 1 at the time of measurement is supplied by current driver 14. The temperature of the Peltier device in diode laser 1 is controlled by temperature controller 15.

In order to control the pressure in sample cell 5 so that it is at a set value below one atmospheric pressure, a flow control unit 18 is provided to the entrance of cell 5 and a pressure control unit 17 and an exhaust pump 16 are provided to the exit of cell 5.

When measurement is carried out, exhaust pump 16 operates at a fixed pumping speed. The necessary pressure is pre-set at pressure control unit 17. The difference between the measured pressure signal and the set pressure signal is fed back to flow control unit 18, and the flow of the gas entering cell 5 is controlled. Because of this design, the pressure in cell 5 can be maintained at a constant value as the gas which is to be measured flows into the cell.

The oscillation wavelength of diode laser 1 can be varied by changing the temperature of the Peltier device or the injection current.

Regarding the mechanism for reducing the pressure of the gas to be measured, in addition to the above described method of controlling the gas flow at the sample cell entrance which introduces the gas to be measured, a method may also be applied wherein the amount of exhaust is controlled by setting flow at the sample cell entrance to a fixed value.

Further, when the wavelength of the light used in spectral analysis is longer than 2.48 $\mu$m and light irradiation for dissociating the clusters in the gas to be measured is needed in addition to the light irradiating from the light source, a light irradiation device 20 may be provided. Light irradiation device 20 is provided to the outside of sample cell 5 and, as a result, light having a photon energy of 0.5 eV or more irradiates the entire sample cell 5. The type of device employed as light irradiation device 20 is optional provided that it can irradiate light having a photon energy of 0.5 eV or more, namely light of wavelength 2.48 $\mu$m or less. For example, a fluorescent lamp which irradiates visible light rays may be used.

Using a device having the above described construction, the absorption spectrum of the gas to be measured and the absorption spectrum of the impurity alone can be simultaneously obtained by scanning the wavelength of the light oscillated from diode laser 1.

Further, if a frequency modulation method wherein the current signal which is input from current driver 14 to diode laser 1 is set to $i=I_0+a\cdot\sin(\omega t)$ wherein the AC component $a\cdot\sin(\omega t)$ is added to the DC component $I_0$, the derivative absorption spectrum can be obtained.

Chopper 3 is used for DC amplification. When measuring the absorption spectrum by injecting the current signal of the DC component only to diode laser 1, modulation of the laser light is carried out at chopper 3 in order to reduce noise. However, when measuring the derivative absorption spectrum by injecting to diode laser 1 a current signal wherein the AC component has been added to the DC component, chopper 3 is not used.

Furthermore, the process of measuring data at calculator 13 may be carried out by first comparing the absorption spectrum which has passed through the gas to be measured and the absorption spectrum which has passed through the gaseous impurity alone. The absorption peak whose absorption wavelength coincides with the absorption peak in the absorption spectrum obtained from the gaseous impurity only can be recognized from among the absorption peaks in the absorption spectrum from the gas to be measured. Programming may be done in advance so that the absorption intensity of this absorption peak is detected and a numerical value is displayed. If this is done, then, it becomes possible to speed up measurement.

An infrared spectroscopic analysis device such as this can be used by directly connecting the sample cell to a pipe arrangement in the production process for semiconductors or the like, and is ideally suited for carrying out the in-situ measurements conveniently during the process.

(Embodiment 1)

The dependence on pressure of the absorption spectrum associated with $H_2O$ was investigated. The device shown in FIG. 1 was employed to measure the absorption spectrum for the sample gas $N_2$ which included a trace moisture content. Further, because the goal was to investigate the effects of pressure on the absorption spectrum, the oscillation wavelength of the diode laser was scanned at around 1.380 $\mu$m, at which it is possible to obtain peaks associated with $H_2O$ having a comparatively large absorption intensity. Moreover, the oscillation wavelength of the diode laser was varied by varying the injection current.

Figure 5:
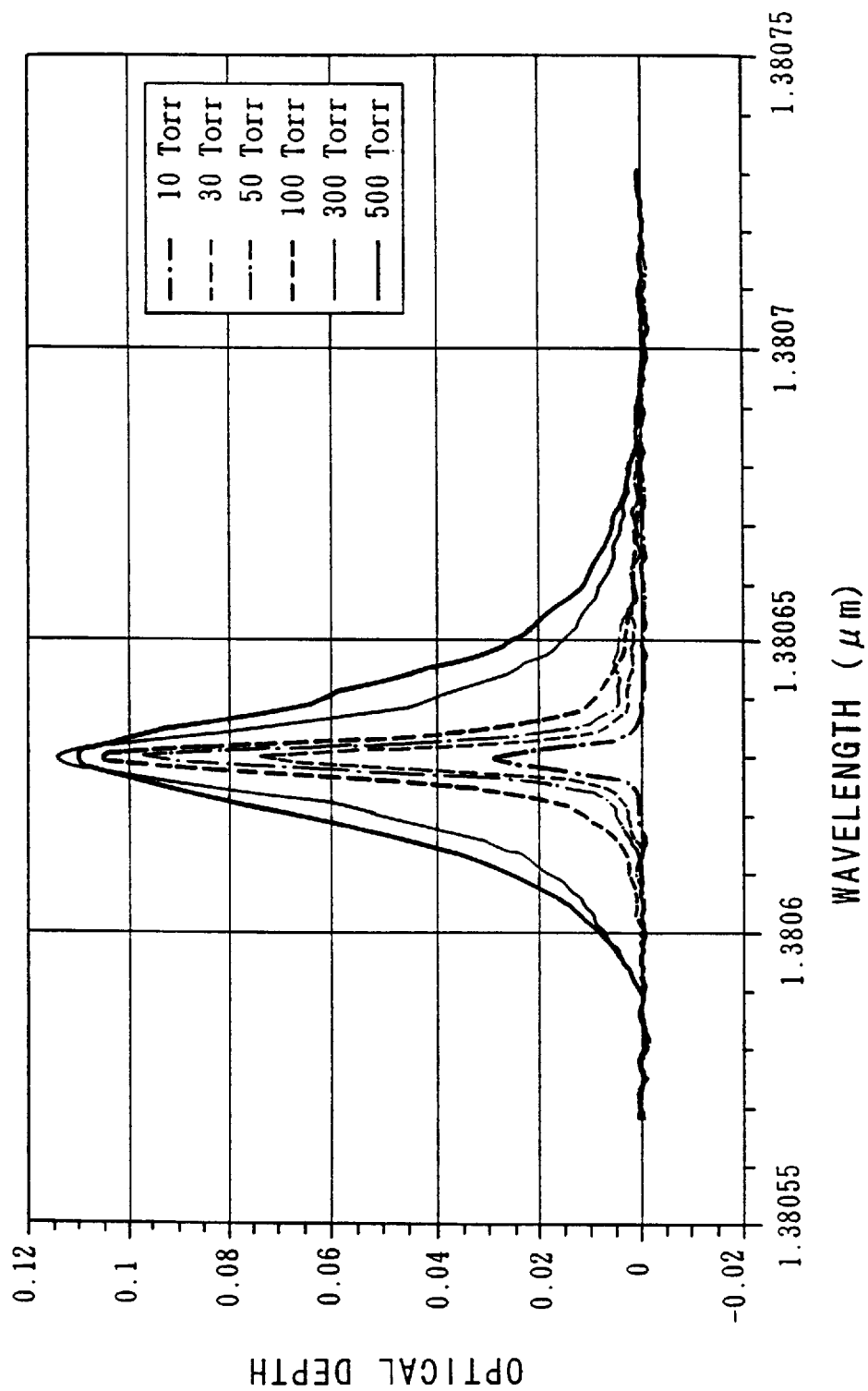
FIG. 5 is a graph showing the dependence on pressure of the absorption spectrum associated with $H_2O$ measured in an embodiment of the present invention.

FIG. 5 shows absorption spectrums obtained by measurements conducted with the sample gas of 100 ppm $H_2O/N_2$ flowing when the pressure inside the sample cell was 10, 30, 50, 100, 300, and 500 Torr respectively. Wavelength is noted along the horizontal axis, while optical depth, which is equivalent to the absorption intensity, is noted along the vertical axis in this graph. As shown in FIG. 5, when the pressure in the sample cell is increased to 300 Torr or higher, the shape of the spectrum is distorted, becoming non-symmetrical, due to the influence of neighboring absorption lines. Further, while the intensity of absorption is expected to be greater at a pressure of 500 Torr than at 300 Torr, in fact, conversely, it is smaller. At pressures of 500 Torr or less, and in particular, at pressures of 300 Torr or less, absorption intensity becomes sequentially smaller as the pressure becomes lower. At the same time, the width of the absorption line spectrum narrows, becoming a symmetrical shape without distortions. From these results, it is clear that it is possible to improve resolution of the measurement by decreasing pressure. However, when the pressure of the sample gas is lowered to 10 Torr or less, there is less reduction in the width of the absorption line and the height of the spectrum becomes low. Accordingly, it is not desirable to reduce pressure under 10 Torr.

From these results, it was recognized that an optimal analysis of the moisture in a gas to be measured could be obtained in a pressure range of 10 to 500 Torr.

(Embodiment 2)

The dependence on pressure of the absorption spectrum associated with $CO_2$ was investigated. The device shown in FIG. 1 was employed to measure the absorption spectrum for the gas to be measured, HCl which included $CO_2$. Further, because the goal was to investigate the effects of pressure on the absorption spectrum, the oscillation wavelength of the diode laser was scanned at around 1.435 $\mu$m (1435 nm), at which it is possible to obtain peaks originating from $CO_2$ having a comparatively large absorption intensity. Moreover, the oscillation wavelength of the diode laser was varied by varying the injection current.

Figure 6:
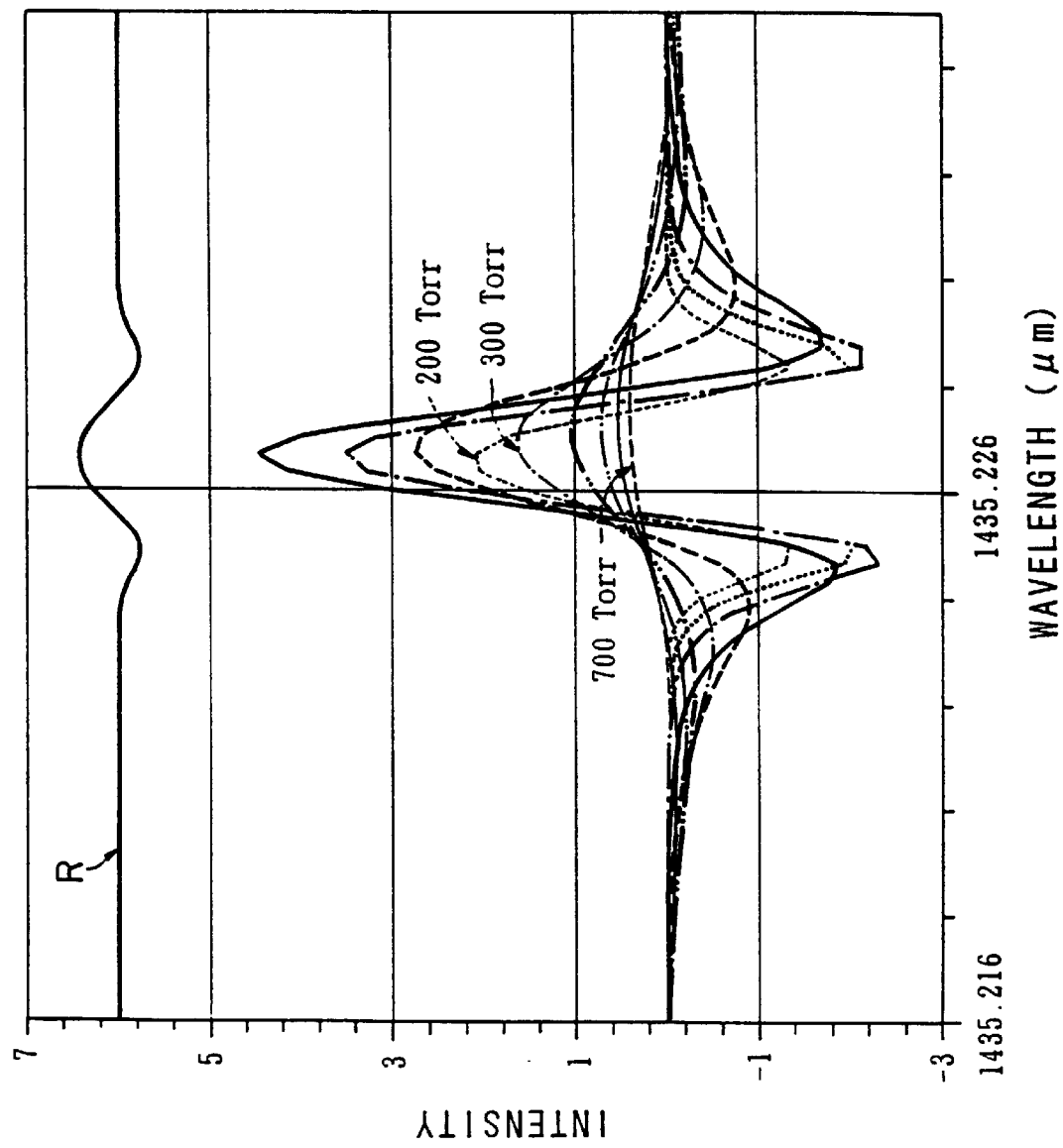
FIG. 6 is a graph showing the dependence on pressure of the derivative absorption spectrum associated with $CO_2$ measured in an embodiment of the present invention.

FIG. 6 shows derivative absorption spectrums obtained by measurements conducted with the sample gas of 7.4% by weight $CO_2/HCl$ flowing when the pressure inside the sample cell was 10, 30, 50, 100, 200, 300, 400, 500, 600, and 700 Torr respectively. The oscillation wavelength is noted along the horizontal axis while the derivative value (arbitrary units) of the change in absorption intensity is noted along the vertical axis in this graph. Further, at the same time, the reference cell was filled with $CO_2$ alone at 20 Torr and measurements were carried out. In FIG. 6, spectrum R for $CO_2$ alone was aligned along the horizontal axis for comparison with the aforementioned derivative value absorption spectrums. Identification was made by recognizing the coincidence of the position (wavelength) of the peak obtained by measuring $CO_2$ alone and the position of the peak obtained by measuring the gas to be measured. Additionally, it is noted here that spectrum R which was obtained by measuring $CO_2$ alone is displayed by compressing the variation in absorption intensity and raising the base line.

Figure 7:
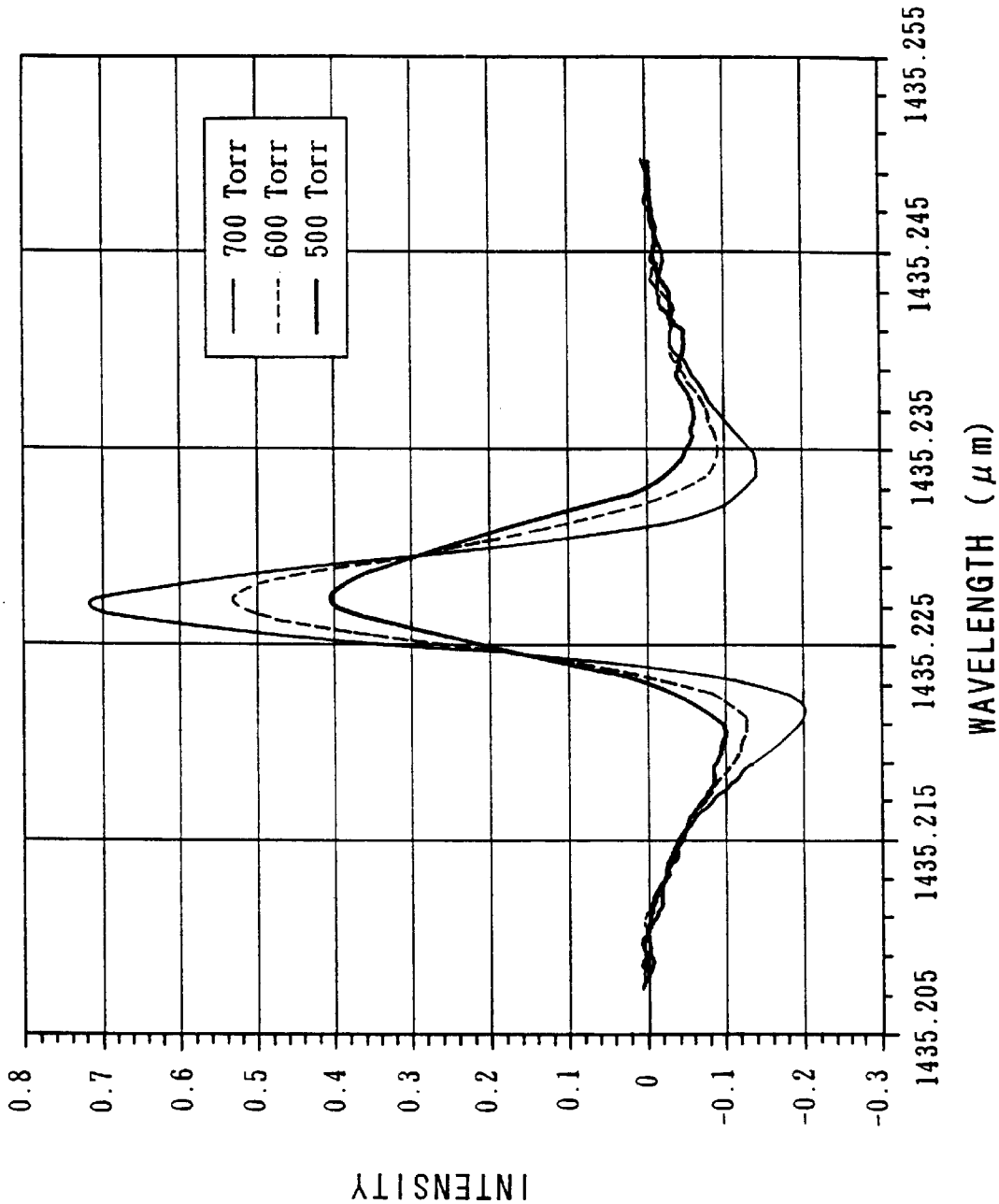
FIG. 7 shows an enlarged portion of the graph in FIG. 6.
Figure 8:
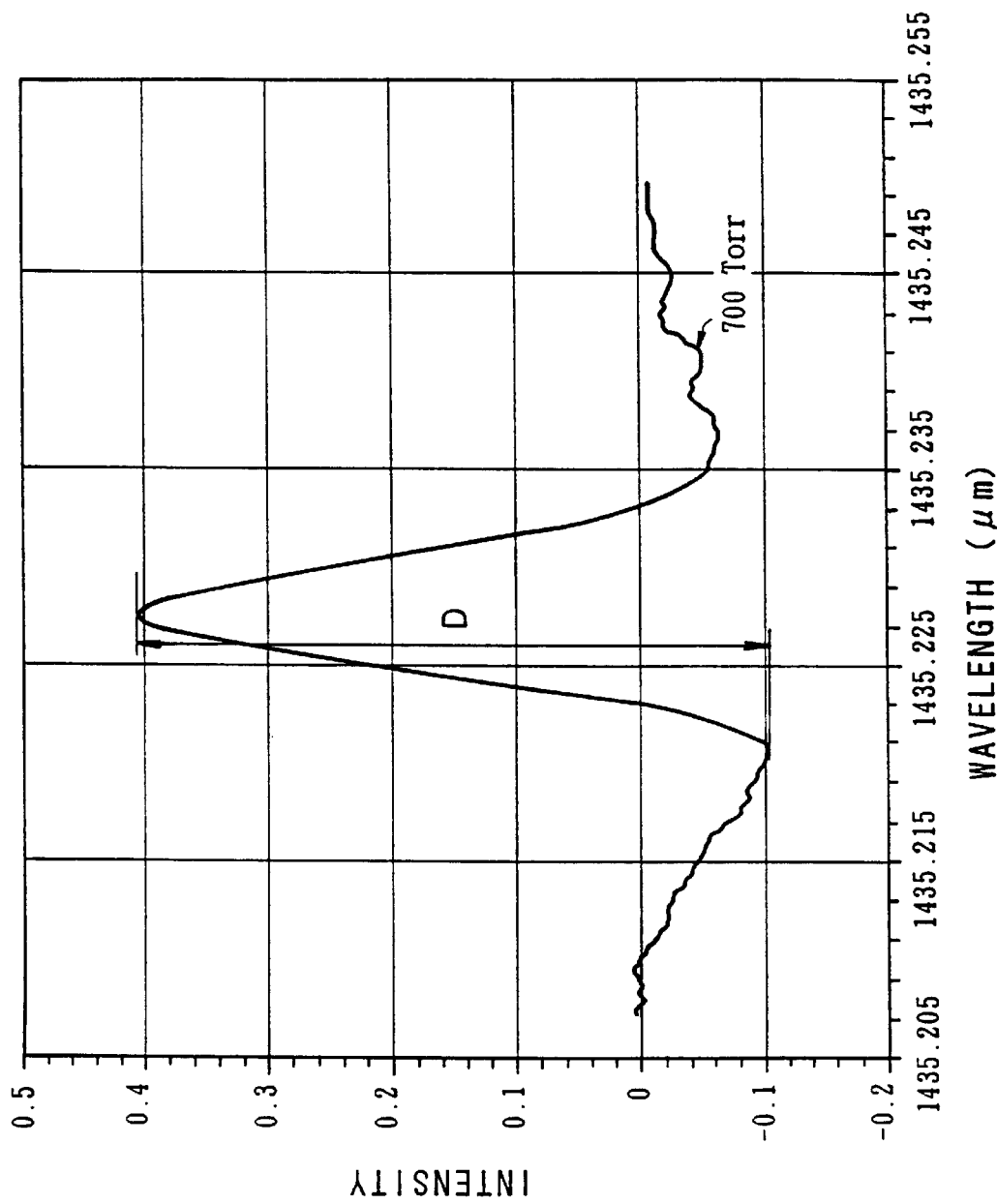
FIG. 8 shows an enlarged portion of the graph in FIG. 6.
Figure 9:
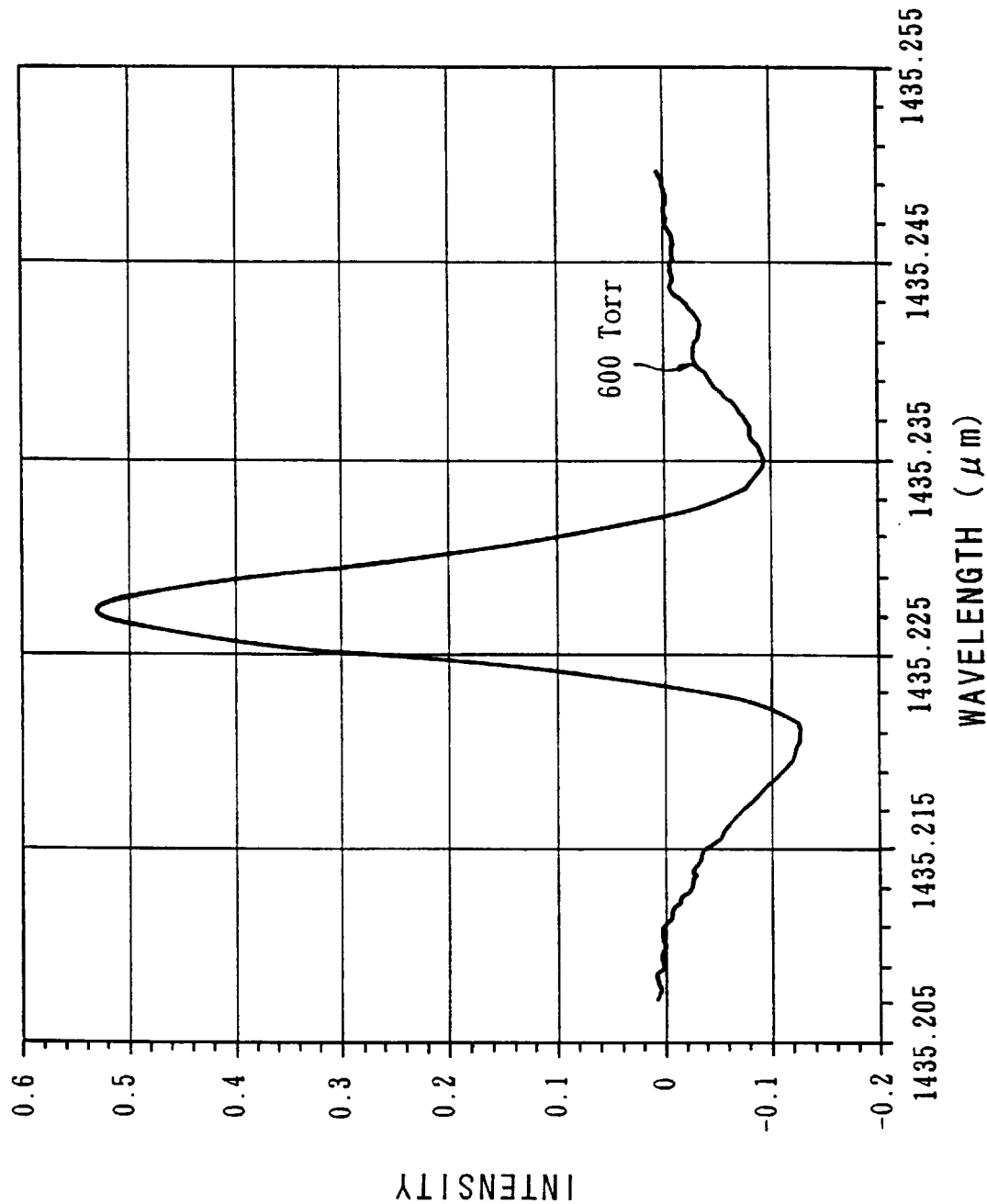
FIG. 9 shows an enlarged portion of the graph in FIG. 6.
Figure 10:
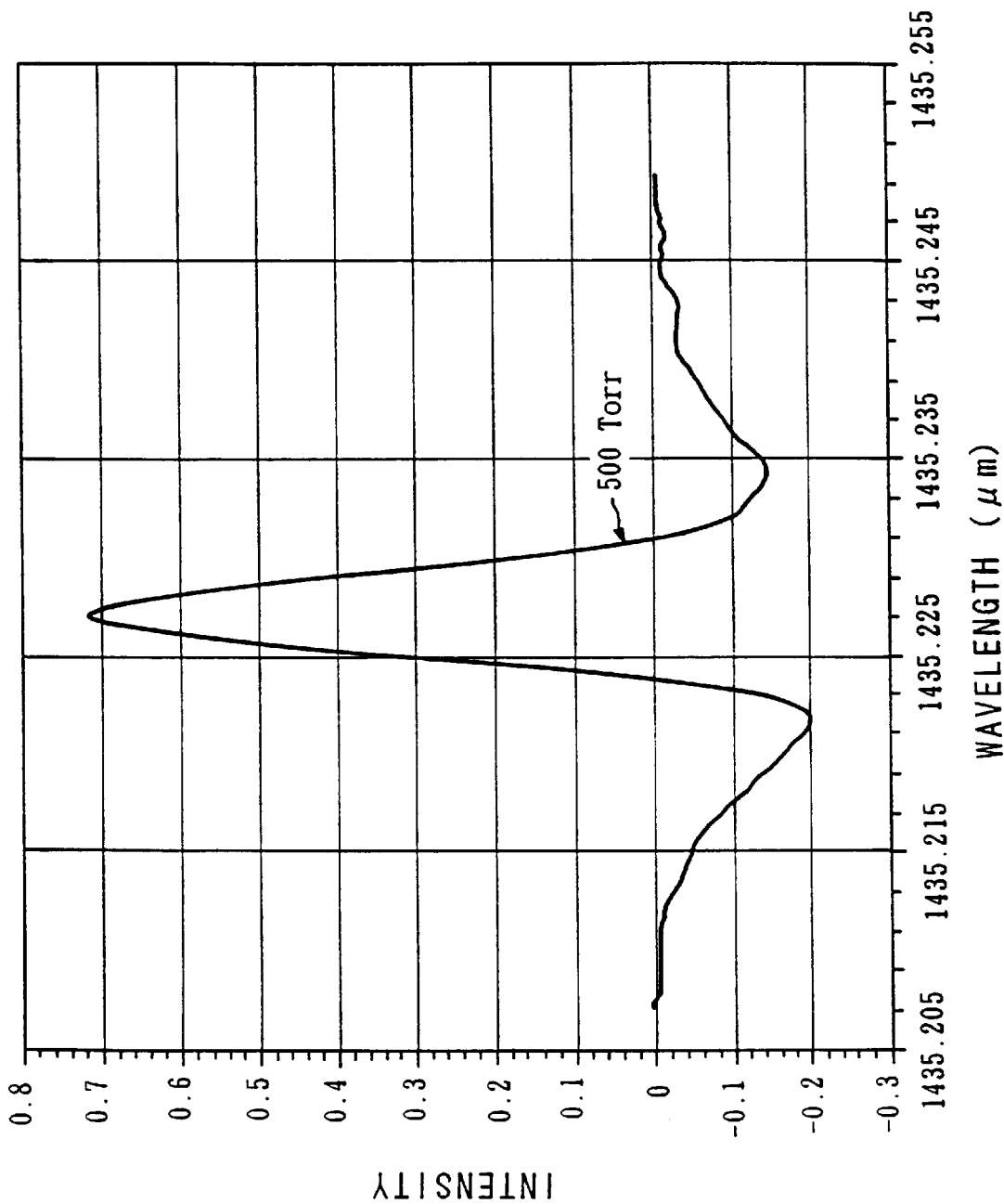
FIG. 10 shows an enlarged portion of the graph in FIG. 6.
Figure 11:
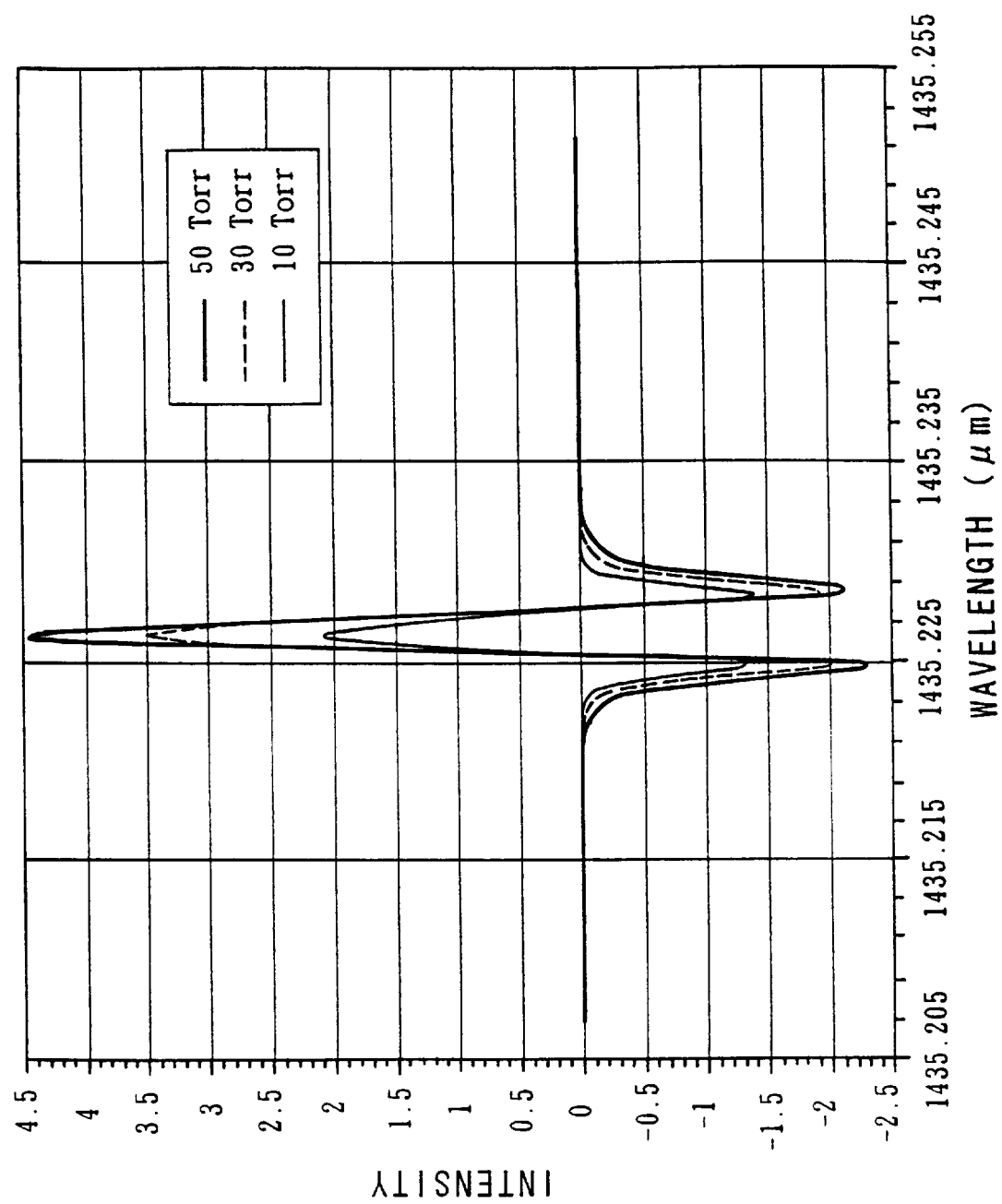
FIG. 11 shows an enlarged portion of the graph in FIG. 6.
Figure 12:
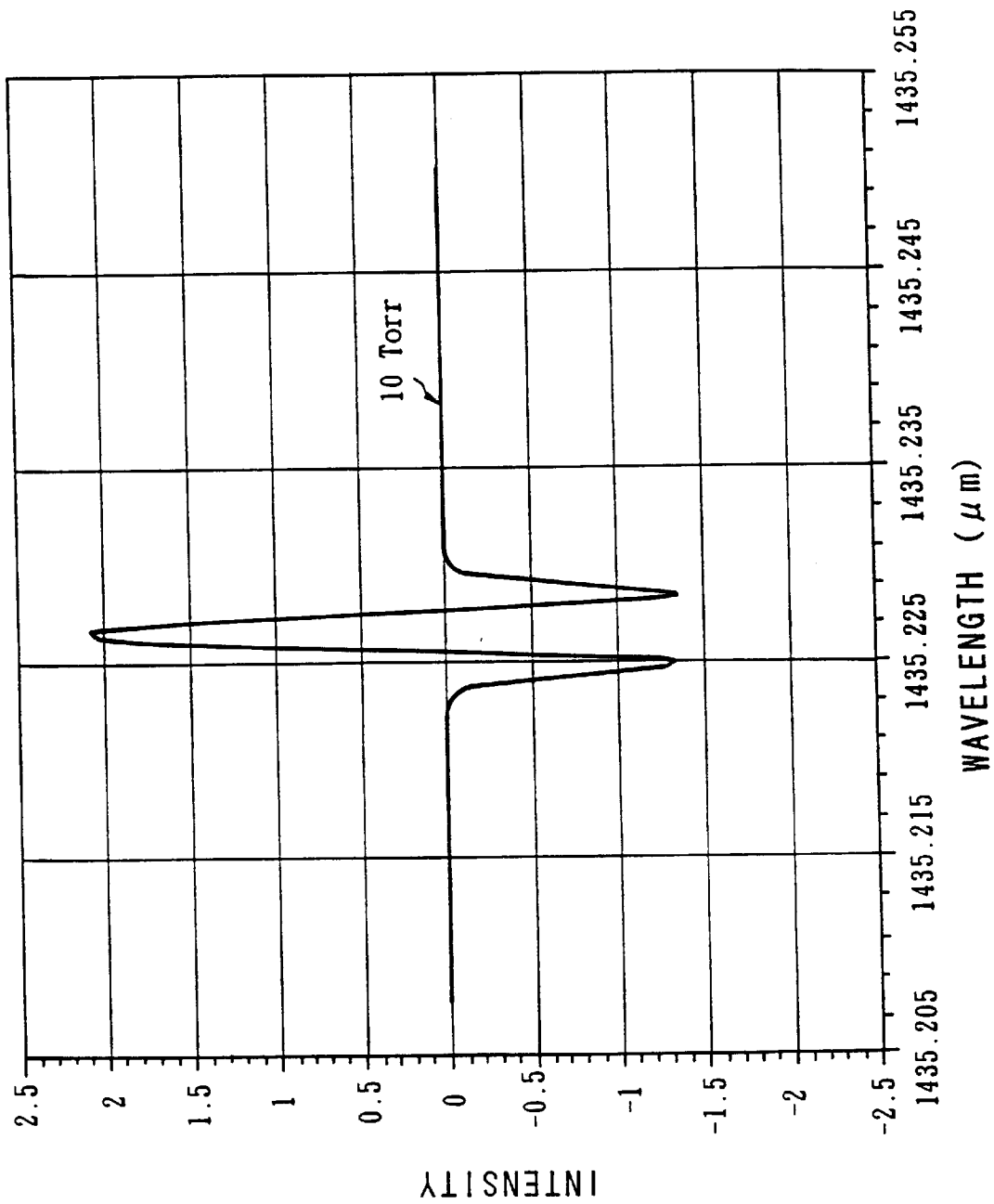
FIG. 12 shows an enlarged portion of the graph in FIG. 6.

Further, in order to be able to easily see the overlap in spectrums, portions of the spectrum shown in FIG. 6 have been enlarged and are shown in FIGS. 7 through 11. FIG. 7 shows the spectrum at the sample gas pressures from 500 to 700 Torr. FIG. 8 shows the spectrum at the sample gas pressure of 700 Torr. FIG. 9 shows the spectrum at the sample gas pressure of 600 Torr. FIG. 10 shows the spectrum at the sample gas pressure of 500 Torr. FIG. 11 shows the spectrum at the sample gas pressures from 10 to 50 Torr. FIG. 12 shows the spectrum at the sample gas pressure of 10 Torr.

When carrying out determination of the impurity using derivative absorption peaks, the distance from the tip of the peak to the lowest point at the bottom where the peak begins to rise (indicated by D in FIG. 8) can be used in the determination as the peak height (absorption intensity).

In this embodiment, as shown in FIGS. 8 through 10, when the pressure of the sample gas is 600 Torr and 700 Torr respectively, the bottom of the signal is disturbed due to noise and it is not possible to perform an accurate determination. At pressures of 500 Torr or less, the effects of noise are absent, and the bottom of the signal is stable and may be used in determination. Further, as shown in FIGS. 11 and 12, stable peaks can be obtained at a 10 Torr or greater sample gas pressure. These may be used to carry out determination with great accuracy.

From these results, it was recognized that an optimal analysis of the $CO_2$ in a gas to be measured could be obtained in a pressure range of 10 to 500 Torr.

(Embodiment 3)

The dependence on pressure of the absorption spectrum associated with $CH_4$ was investigated. The device shown in FIG. 1 was employed to measure the absorption spectrum for the sample gas $N_2$ gas containing $CH_4$. Further, because the goal was to investigate the effects of pressure on the absorption spectrum, the oscillation wavelength of the diode laser was scanned at around 1.645 $\mu$m to 1.646 $\mu$m (1645 nm to 1646 nm), at which it is possible to obtain peaks associated with $CH_4$ having a comparatively large absorption intensity. Moreover, the oscillation wavelength of the diode laser was varied by varying the injection current.

Figure 13:
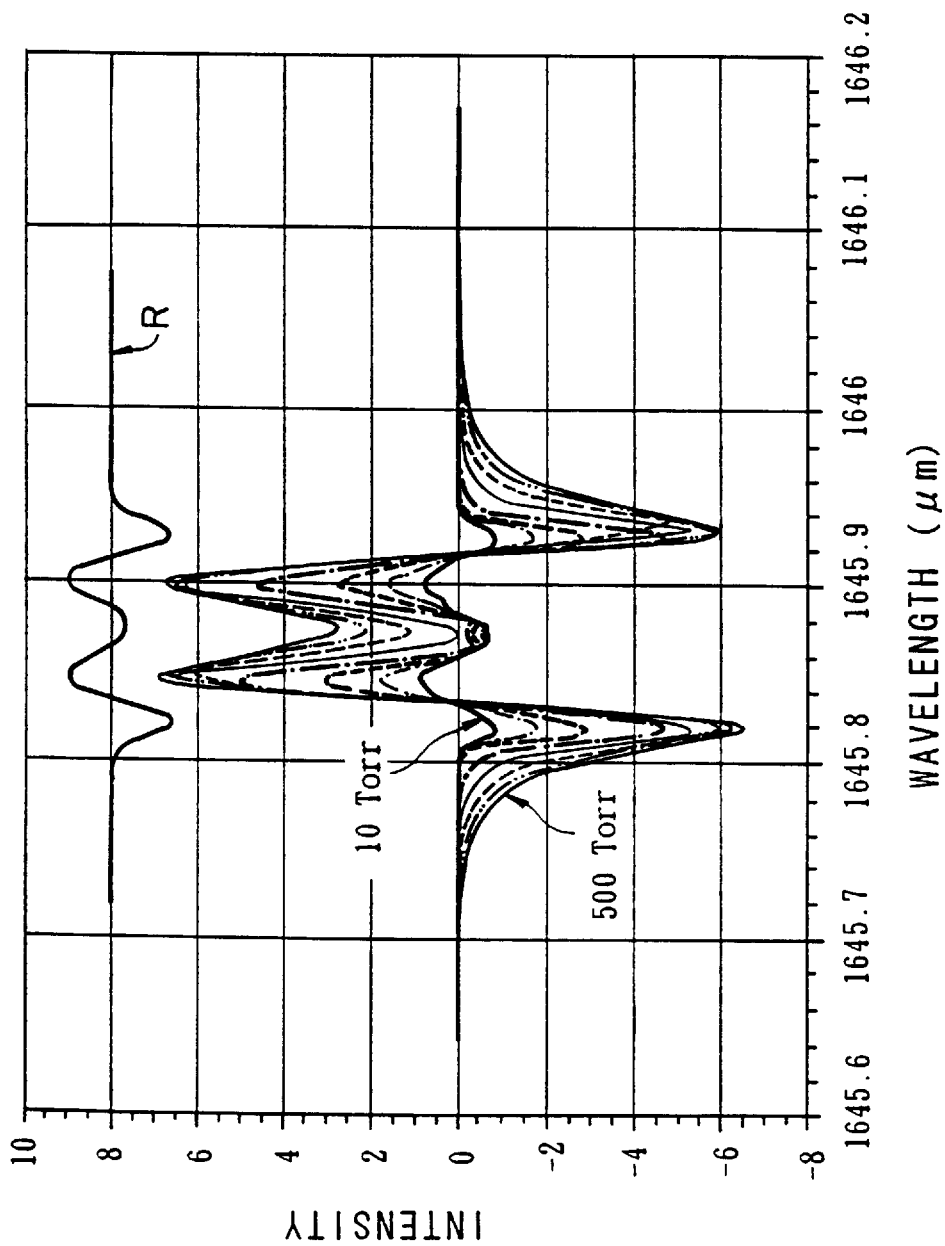
FIG. 13 is a graph showing the dependence on pressure of the derivative absorption spectrum originating from $CH_4$ measured in an embodiment of the present invention.

FIG. 13 shows derivative absorption spectrums obtained by measurements conducted with the sample gas of 7.9% by weight $CH_4/N_2$ flowing when the pressure inside the sample cell was 10, 30, 50, 100, 200, 300, 400, 500, 600, and 700 Torr respectively. The oscillation wavelength is noted along the horizontal axis while the derivative value of the change in absorption intensity is noted along the vertical axis (arbitrary units) in this graph. Further, at the same time, the reference cell was filled with $CH_4$ alone at 20 Torr and measurements were carried out. In FIG. 13, spectrum R for $CH_4$ alone was aligned along the horizontal axis for comparison to the aforementioned derivative absorption spectrums. Identification was carried out by confirming the coincidence of the position (wavelength) of the peak obtained by measuring the $CH_4$ alone and the position of the peak obtained by measuring the gas to be measured. Additionally, it is noted here that spectrum R which was obtained by measuring $CH_4$ alone is displayed by compressing variation in absorption intensity and raising the base line.

Figure 14:
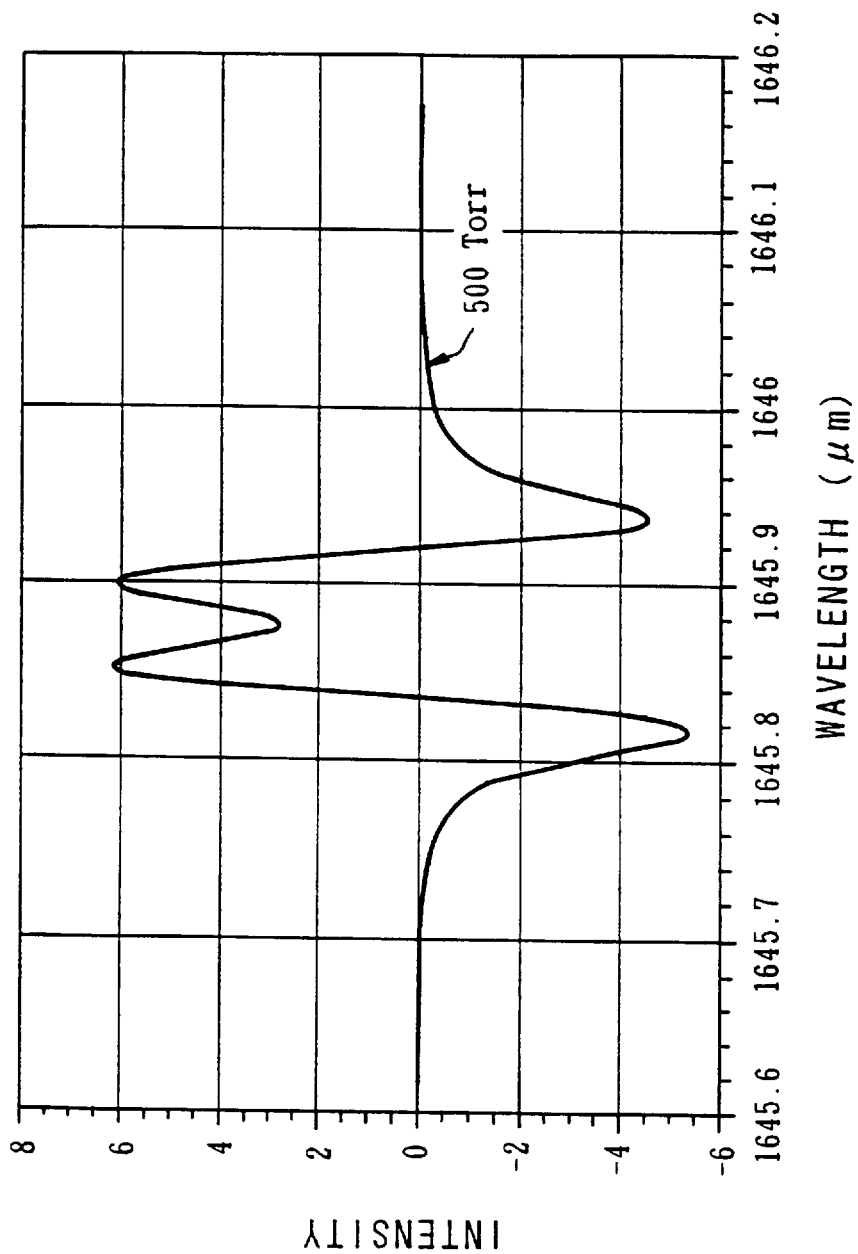
FIG. 14 shows an enlarged portion of the graph in FIG. 13.
Figure 15:
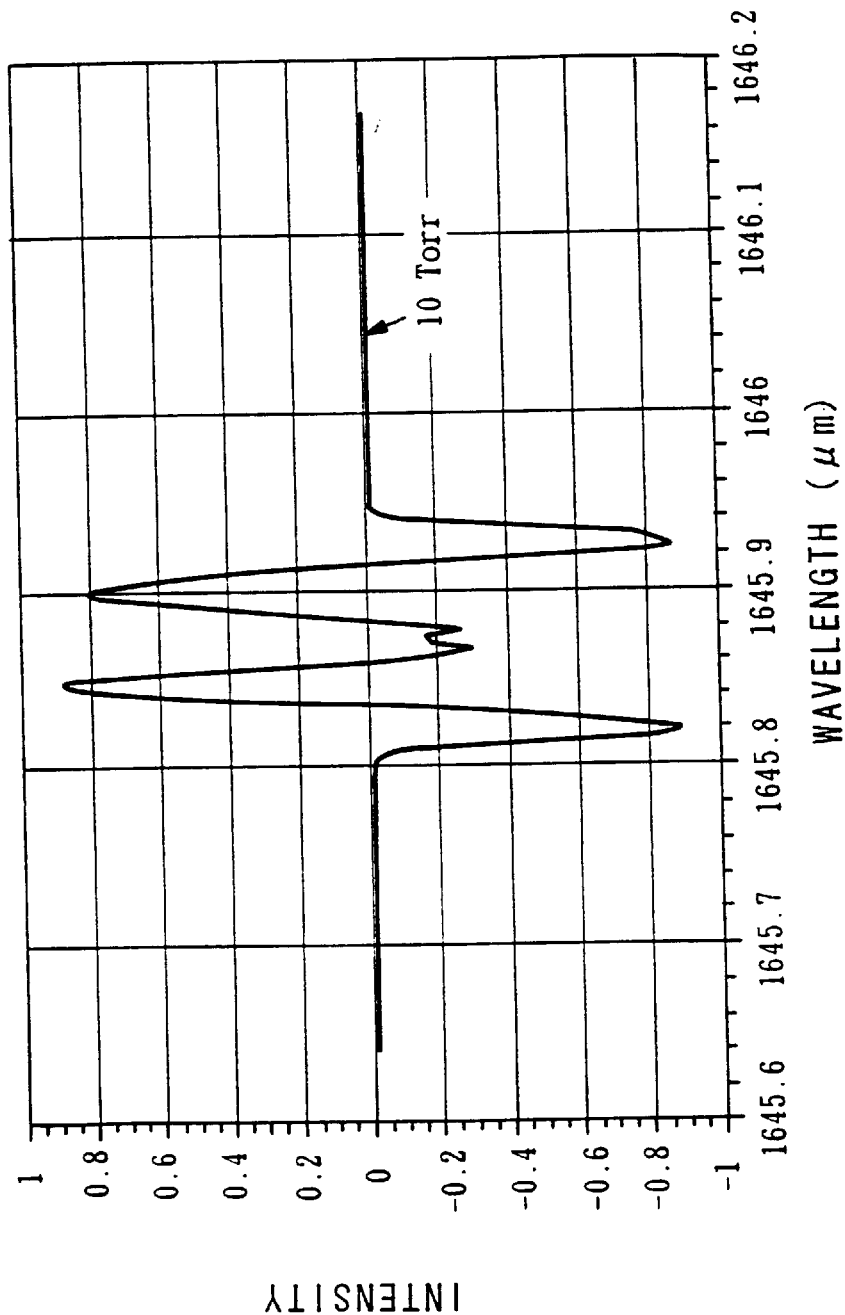
FIG. 15 shows an enlarged portion of the graph in FIG. 13.

Further, in order to be able to easily see the overlap in spectrums, portions of the spectrum shown in FIG. 13 have been enlarged and are shown in FIGS. 14 and 15. FIG. 14 shows the spectrum at a sample gas pressure of 500 Torr, while FIG. 15 shows spectrum R at a pressure of 10 Torr.

Because two peaks lie near each other in the derivative absorption peaks originating from $CH_4$ in this embodiment, detection of peaks is carried out in a state wherein the left cuffs of the peaks on the right side of the graph and the cuffs of the peaks on the left side of the graph overlap. As shown in FIGS. 14 and 15, when the pressure of the sample gas is 500 Torr, and when it is 10 Torr, stable peaks are obtained. These may be used to carry out determination with great accuracy.

From these results, it was recognized that an optimal analysis of $CH_4$ in a gas to be measured can be obtained in a pressure range of 10 to 500 Torr.

(Embodiment 4)

Using the device shown in FIG. 1, the analysis of the moisture in hydrogen chloride gas, a representative example of the gases which are used as material in semiconductor manufacturing, was carried out. The sample cell was filled at 30 Torr with hydrogen chloride gas having an unknown moisture concentration, while the reference cell was filled with a moisture alone at a pressure of 20 Torr. Additionally, the optical path length was 50 cm.

By varying the temperature of the laser by the Peltier device from 20° to 30° C., laser light was scanned in the region of the wavelength from 1.3803 to 1.3814 $\mu$m, and the derivative absorption spectrum was measured. As a result, the spectrum shown in FIG. 16 was obtained.

Figure 16:
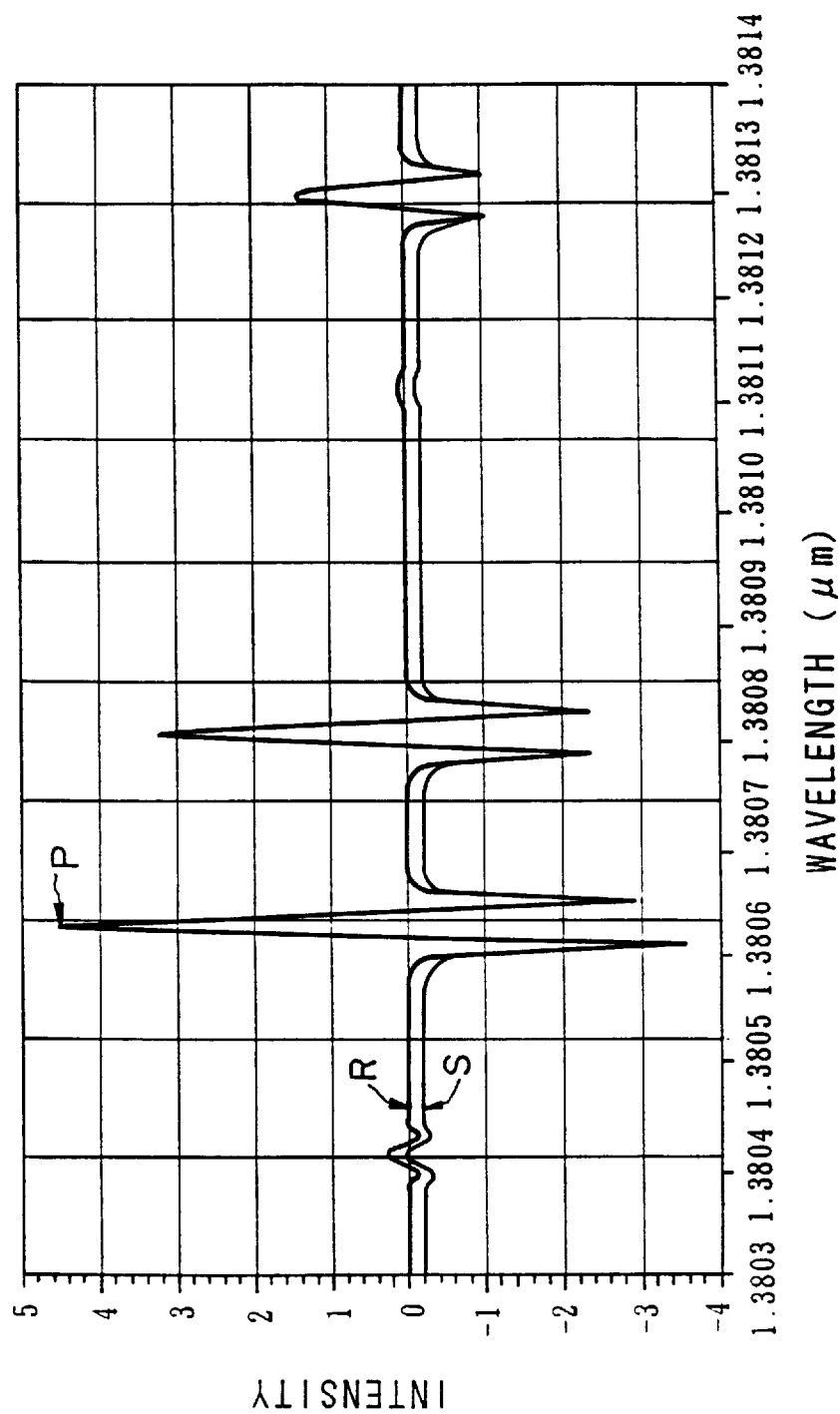
FIG. 16 is a derivative absorption spectrum for $H_2O/HCl$ measured in embodiment of the present invention.

In FIG. 16, oscillation wavelength is shown on the horizontal axis, while the derivative value of the change in absorption intensity is noted along the vertical axis (arbitrary units) in this graph. Further, in order to avoid overlap between the spectrum for the moisture only (indicated by R in the figure) and the spectrum for the sample gas (indicated by S in the figure), the base line for spectrum S for the sample gas was lowered one scale unit.

As shown in FIG. 16, the spectrum for the sample gas could be obtained with the same resolution as that of the spectrum for the moisture only. Accordingly, by comparing the spectrum for the gas to be measured and the spectrum for the moisture alone, and confirming the plurality of absorption peaks originating from water based on the position and intensity ratio of the peaks, the water can be identified with surety. Then, the strongest peak which does not experience any interference from nearby peaks is selected from among the plurality of absorption peaks originating from water, and the determination of the water is then carried out from the absorption intensity of this strongest peak.

Namely, in FIG. 16, there is strong coincidence of four sharp peaks in both the spectrum for the moisture alone and the spectrum for the sample gas containing hydrogen chloride. Further, when the relative intensity at a wavelength of 1.3806 $\mu$m is set to 1, then the intensities at wavelengths of 1.38076 $\mu$m and 1.38113 $\mu$m for the case of the moisture only are, respectively, 0.73 and 0.285. The same values hold in the case of the sample gas as well. By comparing the values of relative intensities of absorption peaks in this way and confirming that the values are the same, it can be determined that the moisture content in the sample gas is responsible for the four peaks in the sample gas, making it possible to carry out the identification of the moisture content accurately.

Additionally, it is noted here that there are no absorption peaks for hydrogen chloride in the region of wavelength employed here, and no peaks other than the aforementioned four peaks can be observed in the sample gas spectrum. For this reason, then, it can be determined that no impurity other than the water is detected in this wavelength region.

Determination of the moisture content is carried out by selecting from among the above four identified peaks, the strongest peak P with no nearby interfering peaks. It can be recognized here that the intensity ratio between strong peak P and the other peaks coincide well between the spectrum for the moisture alone and the spectrum for the sample gas. Accordingly, peak P is a peak arising from the moisture content alone and is judged not to be experiencing interference from unknown peaks. Peak P, then, can be used to carry out determination of the moisture content with surety.

A calibration curve (not noted) is formed in advance showing the relationship between the concentration of the moisture content and the peak intensity based on this strongest peak P. Using this calibration curve, the moisture content in the sample gas is obtained from the strongest peak P in the spectrum of the sample gas.

(Embodiment 5)

Using the device shown in FIG. 1, the analysis of $CO_2$ in hydrogen chloride gas was carried out. The sample cell was filled at 100 Torr with hydrogen chloride gas containing $CO_2$ in the amount of 7.4 wt %, while the reference cell was filled with $CO_2$ alone at a pressure of 20 Torr.

By varying the temperature of the laser by the Peltier device, laser light was scanned in the region of the wavelength from 1.4340 to 1.4358 μm (1434.0 to 1435.8 nm), and the derivative value absorption spectrum was measured. As a result, the spectrum shown in FIG. 17 was obtained.

Figure 17:
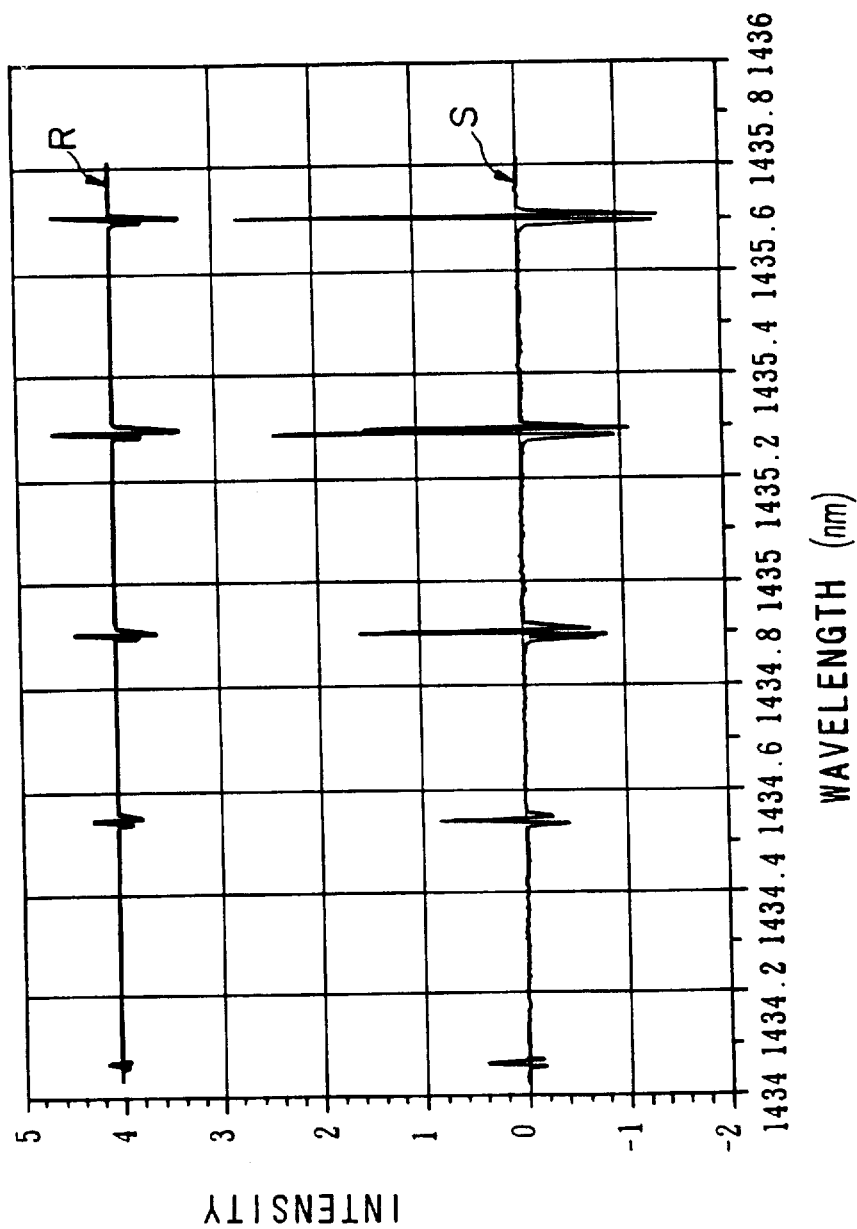
FIG. 17 is a derivative absorption spectrum for $CO_2/HCl$ measured in an embodiment of the present invention.

In FIG. 17, oscillation wavelength is shown on the horizontal axis, while the derivative value of the change in absorption intensity is noted along the vertical axis (arbitrary units) in this graph. Further, in order to avoid overlap between the spectrum for the $CO_2$ by itself (indicated by R in the figure) and the spectrum for the sample gas (indicated by S in the figure), the base line for spectrum R for the $CO_2$ alone was raised.

As shown in FIG. 17, the spectrum S for the sample gas could be obtained with the same resolution as that of the spectrum R for the $CO_2$ alone. Accordingly, by comparing the spectrum of the sample gas and the spectrum of the $CO_2$ alone, and confirming the plurality of absorption peaks associated with $CO_2$ based on peak position and relative intensity values, the $CO_2$ can be identified with certainty.

Further, when the concentration of $CO_2$ is unknown, the strongest peak which does not experience any interference from nearby peaks is selected from among the plurality of absorption peaks associated with $CO_2$, and the determination of the $CO_2$ is then carried out in the same manner as in the above Embodiment 4. In this embodiment, the peak obtained at a wavelength of 1.3457 μm is desirably used in the determination process since it shows strong absorption intensity.

(Embodiment 6)

Using the device shown in FIG. 1, the analysis of $CO_2$ in nitrogen gas was carried out. The sample cell was filled at 100 Torr with nitrogen gas containing $CO_2$ in the amount of 7.4% by weight, while the reference cell was filled with $CO_2$ alone at a pressure of 20 Torr.

By varying the temperature of the laser by the Peltier device, laser light was scanned in the region of the wavelength from 1.4340 to 1.4358 μm (1434.0 to 1435.8 nm), and the derivative absorption spectrum was measured. As a result, the spectrum shown in FIG. 18 was obtained.

Figure 18:
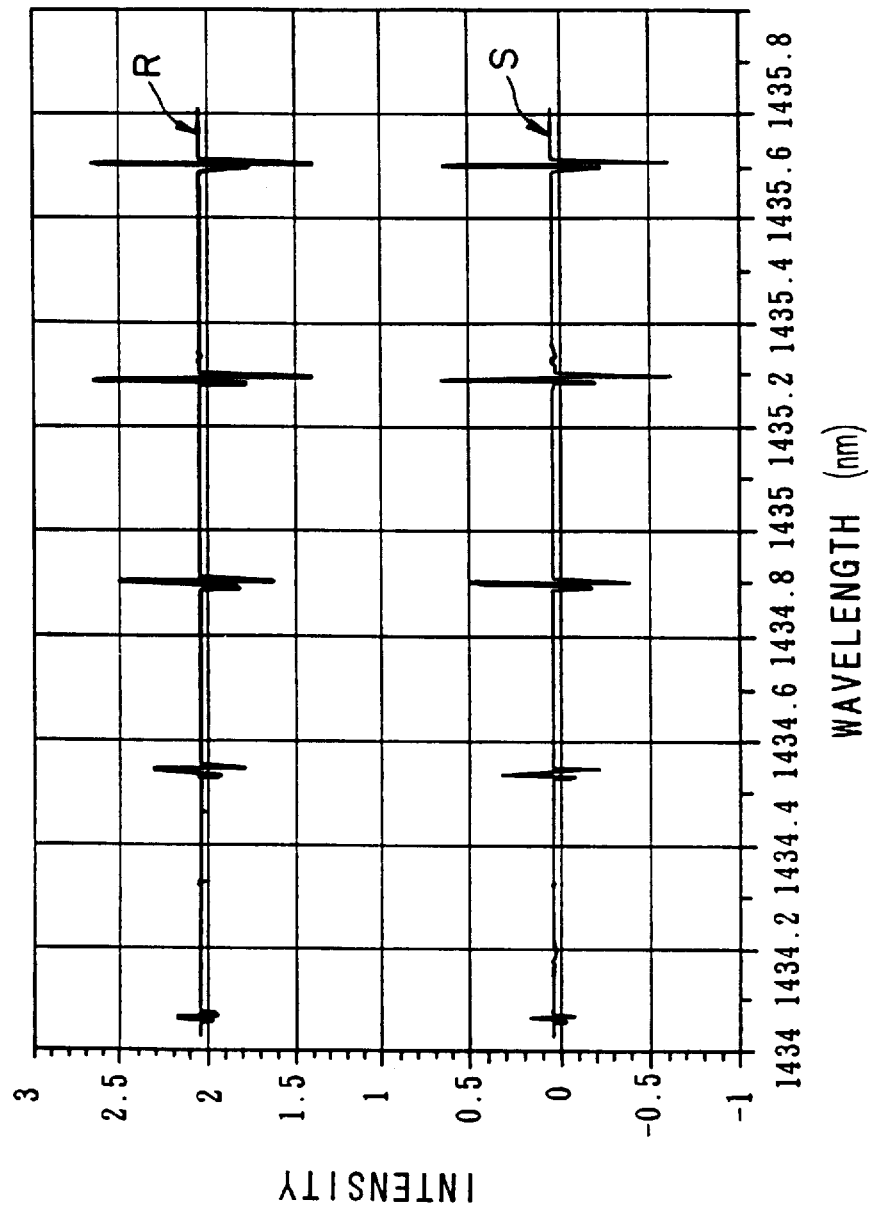
FIG. 18 is a derivative absorption spectrum for $CO_2/N_2$ measured in an embodiment of the present invention.

In FIG. 18, oscillation wavelength is shown on the horizontal axis, while the derivative value of the change in absorption intensity is noted along the vertical axis (arbitrary units) in this graph. Further, in order to avoid overlap between the spectrum for the $CO_2$ alone (indicated by R in the figure) and the spectrum for the sample gas (indicated by S in the figure), the base line for spectrum R for the $CO_2$ alone was raised.

As shown in FIG. 18, the spectrum S for the sample gas could be obtained with the same resolution as that of the spectrum R for the $CO_2$ alone. Accordingly, by comparing the spectrum for the sample gas and the spectrum for the $CO_2$ alone, and confirming the plurality of absorption peaks associated with $CO_2$ based on peak position and relative intensity values, the $CO_2$ can be identified with certainty.

Further, when the concentration of $CO_2$ is unknown, the strongest peak which does not experience any interference from nearby peaks is selected from among the plurality of absorption peaks associated with $CO_2$, and the determination of $CO_2$ is then carried out in the same manner as in the above Embodiment 4. In this embodiment, the peak obtained at a wavelength of 1.3453 μm is desirably used in the determination process since it shows strong absorption intensity.

(Embodiment 7)

Figure 19:
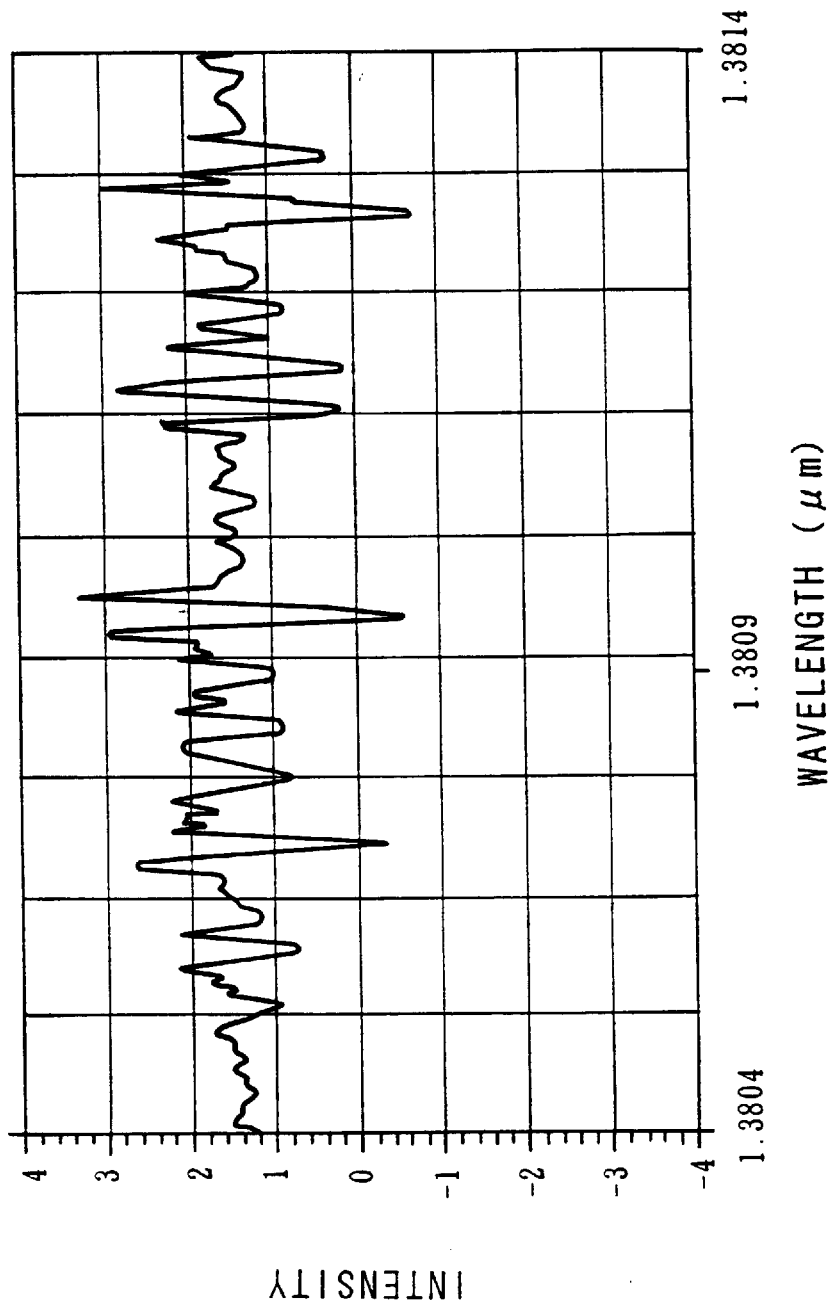
FIG. 19 is a derivative absorption spectrum for $SiH_4$ measured in an embodiment of the present invention.

The sample cell was filled at 30 Torr with $SiH_4$, and measurement was carried out in the same way as in the above embodiment 4. The derivative absorption spectrum obtained is shown in FIG. 19. A plurality of sharp peaks originating from $SiH_4$ in the wavelength range of 1.3804 to 1.3814 μm can be observed. It was determined that these could be used to carry out the identification and determination of $SiH_4$ in the same manner as performed above for the cases of $H_2O$ and $CO_2$.

(Embodiment 8)

Using the device shown in FIG. 1, infrared spectroscopic analysis of a sample gas in which clusters had formed was performed.

Variation in the shift amount of the absorption peak wavelength was investigated by changing the output power of the diode laser and the pressure of the sample gas.

Hydrogen chloride gas containing moisture in the amount of 70 ppm was used as the sample gas. From among the absorption peaks by irradiating the sample gas with laser light, the absorption peak arising from the moisture component and having a standard position at wavelength of 1.38075 μm was investigated. Because the photon energy of the light of wavelength of 1.38075 μm was, at approximately 0.9 eV, larger than 0.5 eV, it was not necessary to provide irradiation light for cluster dissociation in addition to the irradiation light for spectral analysis.

The oscillation wavelength was scanned by fixing the output of the diode laser and varying the temperature of the diode laser. Measurements were then conducted to determine where the peak having a standard position at a wavelength of 1.38075 μm from among the four peaks associated with $H_2O$ shown in FIG. 2 was obtained under the above-described conditions. That is to say, measurements were made to determine how far the peak had shifted from 1.38075 μm. Measurements were carried out with the sample gas under pressures of 50 Torr, 100 Torr and 200 Torr, respectively.

Additionally, it is noted here that the power (output) of the diode laser was set to three levels of 0.7 mW, 1.3 mW and 2.05 mW.

Methods which may be used here for lowering the pressure of the sample gas include a method for controlling the quantity of gas flow at the sample cell 3 entrance through which the sample gas is introduced, or a method for controlling the exhaust amount at the cell exit by fixing the gas flow at the sample cell 3 entrance. Thus, as a result, the pressure in the cell is controlled and maintained as the sample gas flows into sample cell 3. It is noted here that measurement is carried out at room temperature.

Figure 20:
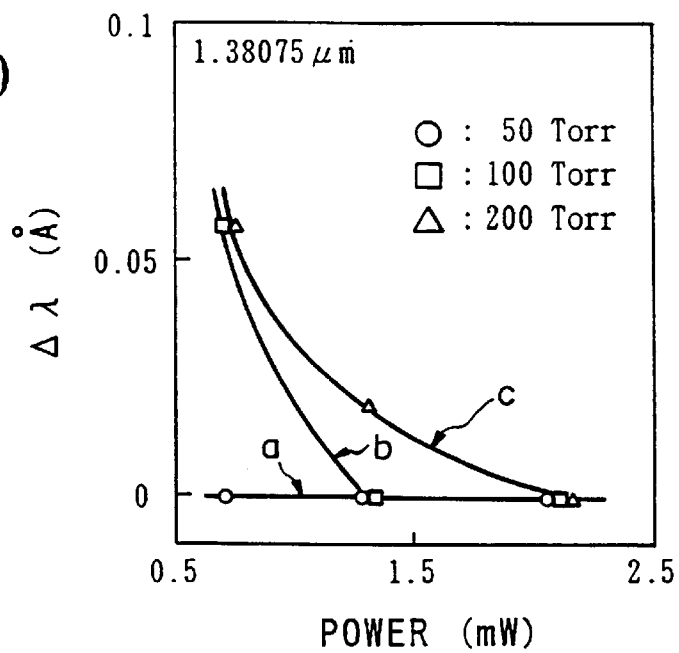
FIG. 20 is a graph showing the results from an embodiment of the present invention depicting the change in the amount of shift of the absorption peak wavelength when the pressure of the sample gas and the irradiated power of the diode laser are varied.

The results are shown in FIG. 20. The power of the diode laser is displayed on the horizontal axis, while the amount of wavelength shift of the peaks for which 1.38075 μm is the standard are respectively shown on the vertical axis. In FIG. 20, a indicates a sample gas pressure of 50 Torr, b indicates a sample gas pressure of 100 Torr, and c indicates a sample gas pressure of 200 Torr.

As shown in FIG. 20, when the pressure of the sample gas is 50 Torr the wavelength does not shift even if the laser power varies. However, when the pressure is 100 Torr, the laser power is low and the wavelength shift is large. Further, when the pressure is 200 Torr, wavelength shifts occur across the entire measurement range, with the amount of shift as large as that which occurs when the laser power is low.

Figure 21:
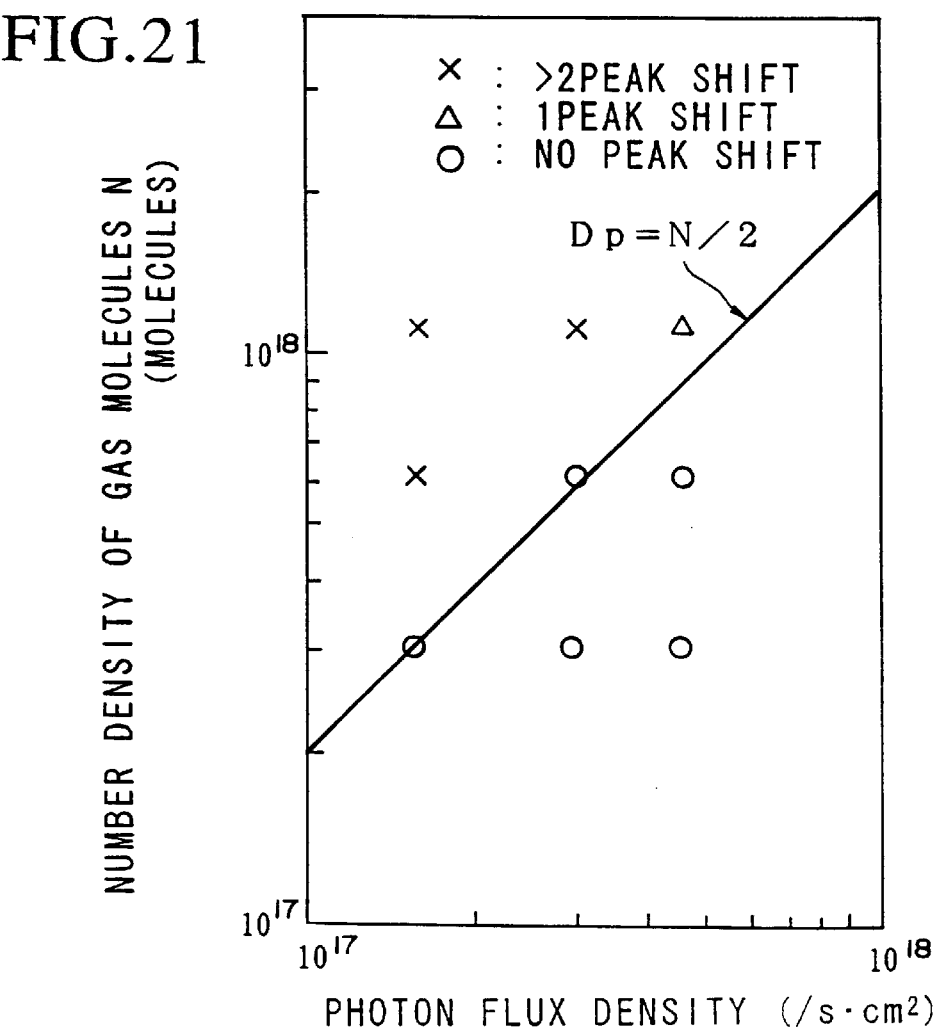
FIG. 21 is a graph showing the results from an embodiment of the present invention depicting the relationship between photon flux density of the irradiating light, the density of the molecules in the sample gas, and shift in the absorption peak.
Figure 22:
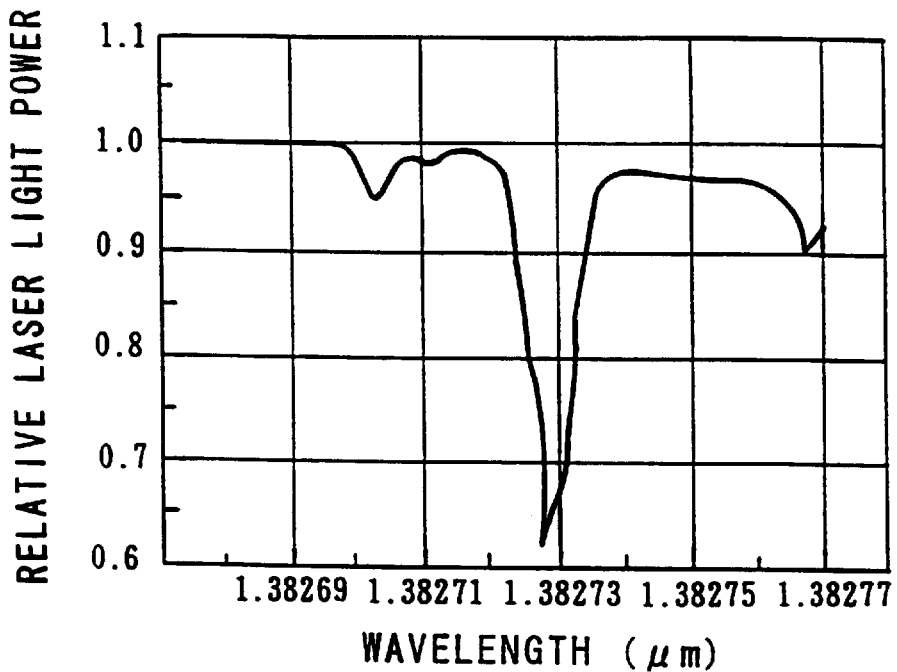
FIG. 22 is an example of the absorption spectrum of moisture measured using a moisture content analysis method of the conventional art.
Figure 23:
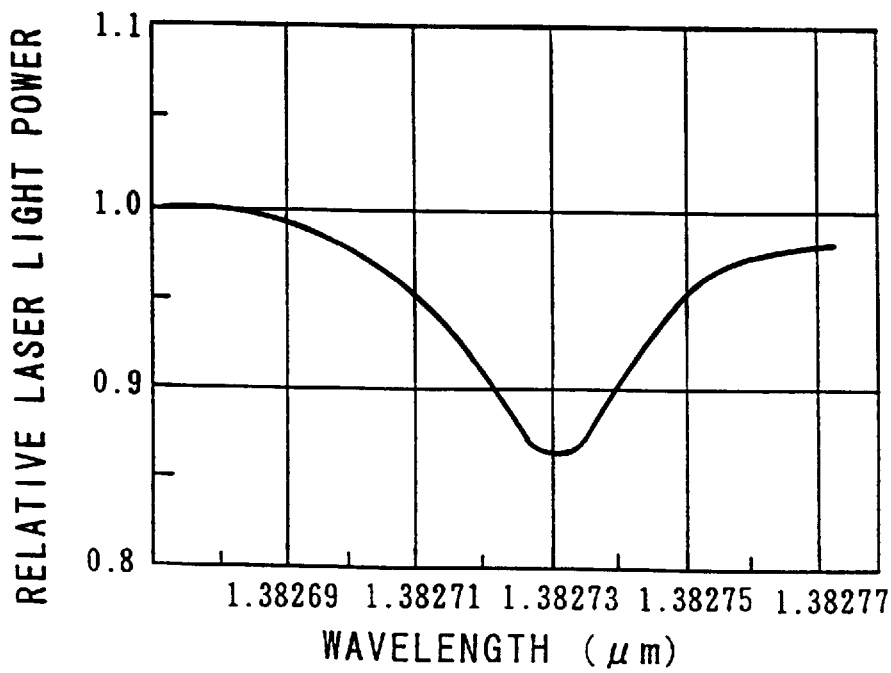
FIG. 23 is an example of the absorption spectrum of nitrogen gas containing moisture measured using a moisture content analysis method of the conventional art.
Figure 24:
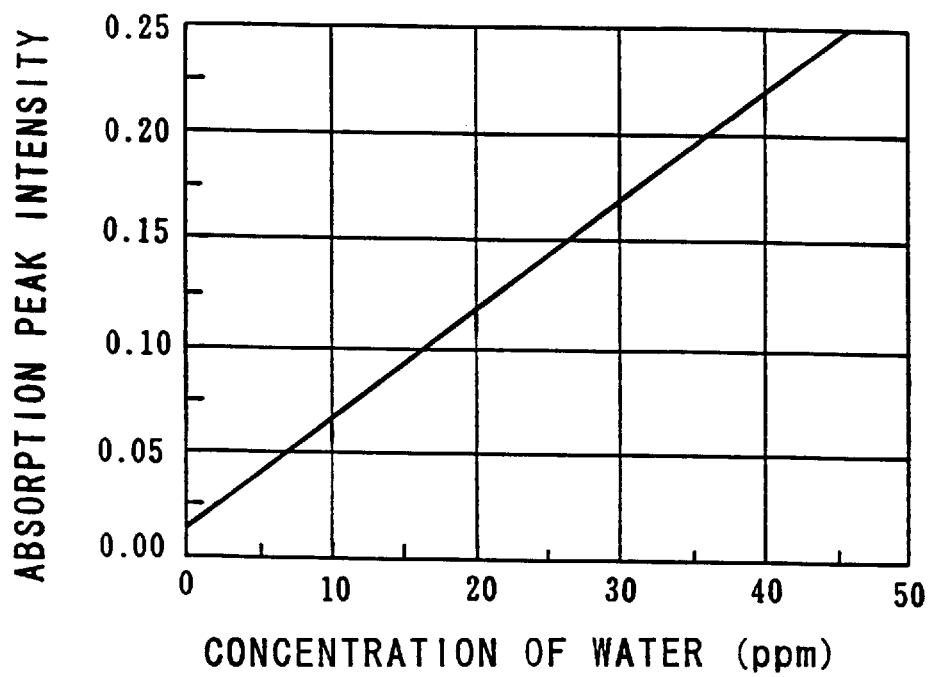
FIG. 24 is an example of the calibration curve showing the relationship between absorption peak intensity and concentration of the moisture content in a moisture content analysis method of the conventional art.

Further, measurements were carried out in the same way on the three peaks caused by $H_2O$ other than the peak having as a wavelength of 1.38075 μm as it standard position. The irradiation density of the irradiation light and the number of molecules in the sample gas was calculated. The relationship between these values and wavelength shift is shown in FIG. 21. In FIG. 21, the photon flux density $D_p$ (number of photons/sec·cm$^2$) of the light from the laser is shown on the horizontal axis, while the number of molecules N in the sample gas is shown on the vertical axis. The symbol "O" indicates the case where none of the four peaks shown in FIG. 21 shifted; the symbol "Δ" indicates the case where a shift could be determined for one of the four peaks shown in FIG. 21; and the symbol "X" indicates the case where a shift could be determined for two or more of the four peaks shown in FIG. 21.

From the results shown in FIG. 21, it was determined that wavelength shifts do not occur in the region wherein $D_p \geq N/2$.

Additionally, it is noted that the photon flux density $D_p$ of the laser light irradiating the sample gas is calculated from the laser light intensity introduced to the sample cell and the laser beam diameter (2 mm).

Furthermore, regarding the number of molecules N in the sample gas which was irradiated by the laser light, because the average speed of the sample gas molecules in sample cell 3 at room temperature (25° C.) is more than six orders of magnitude slower than the speed of light, the density of molecules N present in volume V (cell length: 50 cm; beam diameter: 2 mm) through which the laser light passes is calculated from gas state equation PV=nRT (where pressure, P=50 Torr, 100 Torr and 200 Torr; temperature, T=25° C.; and R is a constant).

By irradiating with light in which the photon energy is 0.5 eV or greater so as to satisfy $D_p \geq N/2$, the possibility of a shift in the absorption peak wavelength can be eliminated. As a result, it is possible to stabilize and carry out an accurate analysis.

Industrial Field of Application

Accordingly to the present invention as described above, a determinative analysis of trace amounts of an impurity in a gas to be measured can be carried out with high sensitivity and high accuracy using infrared spectroscopic analysis.

The present invention can be optimally used in the analysis of a variety of impurities in a gas. However, by carrying measurement out on the premises, the present invention is particularly applicable to the rapid and convenient analysis by the in-situ measurement of trace amounts of an impurity present in gases used as materials for semiconductor manufacturing for which an accurate analysis has conventionally been very difficult, and to the obtaining of highly reliable data.

What is claimed is:

1. An infrared spectroscopic analysis method for gases, for analyzing an impurity in a gas to be measured, comprising the steps of:

measuring absorption intensity by passing light in the infrared region through the gas to be measured, wherein the gas to be measured is analyzed in a low pressure state;

dissociating clusters formed by molecules of the impurity of the gas to be measured; and satisfying the equation $Dp \geq N/2$, wherein Dp (photon number/sec·cm$^2$) is photon flux density with respect to the gas to be measured of the light having a photon energy of 0.5 eV or greater, and N is density of gas molecules in the gas to be measured;

wherein said light has a photon energy of 0.5 eV or greater;

wherein the pressure of the gas to be measured is from 10 to 500 Torr.

2. An infrared spectroscopic analysis method for gases according to claim 1, wherein the gas to be measured is at least one selected from the group consisting of nitrogen, oxygen, argon, helium, carbon dioxide, silane, phosphene, arsine, trichlorosilane, hydrogen chloride and organometallic compounds, and the impurity is one selected from the group consisting of water, carbon dioxide, carbon monoxide, hydrogen fluoride, hydrogen chloride, hydrogen bromide, hydrogen iodide, monosilane, methane and compounds having an —OH group.

3. An infrared spectroscopic analysis method for gases according to claim 1, wherein the absorption spectrum is measured by scanning the wavelength of the light to be passed through the gas to be measured in the range from 1.19 to 2.00 μm.

4. An infrared spectroscopic analysis method for gases according to claim 3, wherein the impurity is water and the wavelength of the light to be passed through the gas to be measured is scanned in the region from 1.35 to 1.42 μm.

5. An infrared spectroscopic analysis method for gases according to claim 3, wherein the impurity is carbon dioxide and the wavelength of the light to be passed through the gas to be measured is scanned in the region from 1.43 to 1.46 μm.

6. An infrared spectroscopic analysis method for gases according to claim 3, wherein the impurity is methane and the wavelength of the light to be passed through the gas to be measured is scanned in the region from 1.29 to 1.50 μm.

7. An infrared spectroscopic analysis method for gases according to claim 3, wherein the impurity is monosilane and the wavelength of the light to be passed through the gas to be measured is scanned in the region from 1.19 to 2.00 μm.

8. An infrared spectroscopic analysis method for gases according to claim 3, wherein the impurity is hydrogen fluoride and the wavelength of the light to be passed through the gas to be measured is scanned in the region from 1.25 to 1.35 μm.

9. An infrared spectroscopic analysis method for gases according to claim 3, wherein the impurity is hydrogen bromide and the wavelength of the light to be passed through the gas to be measured is scanned in the region from 1.34 to 1.37 μm.

10. An infrared spectroscopic analysis method for gases according to claim 3, wherein the impurity is a compound having an —OH group and the wavelength of the light to be passed through the gas to be measured is scanned in the region from 1.40 to 1.45 μm.

11. An infrared spectroscopic analysis device, comprising:

a wavelength tunable diode laser that oscillates infrared region light;

means for passing light oscillated from the laser through a gas to be measured;

means for measuring the intensity of the laser light which has passed through the gas to be measured, wherein infrared spectroscopy is used to analyze an impurity in the gas to be measured;

means for lowering the pressure of the gas to be measured;

means for irradiating the gas to be measured with light having a photon energy of 0.5 eV or greater: and means for measuring a derivative absorption spectrum as the absorption spectrum by detecting a derivative of the change in absorption intensity.

12. An infrared spectroscopic analysis device according to claim 11, further comprising:

means for branching the light oscillated from the diode laser and passing a first portion of the branched light through the gas to be measured while passing a second portion of the branched light through the gaseous impurity alone; and means for respectively measuring the absorption spectrum of the light passed through the gas to be measured and the absorption spectrum of the light which passed through the gaseous impurity alone.

* * * * *